(12) United States Patent
Malamas et al.

(10) Patent No.: US 6,569,873 B2
(45) Date of Patent: May 27, 2003

(54) AZOLIDINES AS BETA-3 ADRENERGIC RECEPTOR AGONISTS

(75) Inventors: Michael Sotirios Malamas, Jamison, PA (US); Elwood Eugene Largis, Nanuet, NY (US); Iwan Gunawan, Somerset, NJ (US); Zenan Li, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/227,225

(22) Filed: Aug. 23, 2002

(65) Prior Publication Data

US 2003/0055079 A1 Mar. 20, 2003

Related U.S. Application Data

(62) Division of application No. 09/904,161, filed on Jul. 12, 2001, now Pat. No. 6,465,501.
(60) Provisional application No. 60/218,706, filed on Jul. 17, 2000.

(51) Int. Cl.$^7$ ...................... C07D 417/12; A61K 31/44; A61P 3/08
(52) U.S. Cl. ....................... 514/341; 514/342; 514/376; 514/377; 546/270.7; 546/271.4; 546/274.4; 546/274.7; 548/226; 548/233; 548/234
(58) Field of Search ............ 546/270.7, 271.4, 546/274.4, 244.7; 514/341, 342

(56) References Cited

U.S. PATENT DOCUMENTS

| | | |
|---|---|---|
| 4,526,786 A | 7/1985 | Bourgery et al. |
| 4,813,998 A | 3/1989 | Van Lommen et al. |
| 5,153,210 A | 10/1992 | Ainsworth et al. |
| 5,561,142 A | 10/1996 | Fisher et al. |
| 5,578,620 A | 11/1996 | Fujita et al. |
| 5,614,523 A | 3/1997 | Audia et al. |
| 5,741,789 A | 4/1998 | Hibschman et al. |
| 5,786,356 A | 7/1998 | Bell et al. |
| 5,789,402 A | 8/1998 | Audia et al. |
| 5,998,452 A | 12/1999 | Ohi et al. |
| 6,069,176 A | 5/2000 | Tsuchiya et al. |
| 6,150,378 A | 11/2000 | Chatterjee et al. |
| 6,214,842 B1 | 4/2001 | Malamas et al. |
| 6,288,231 B1 | 9/2001 | Chatterjee et al. |
| 6,346,532 B1 | 2/2002 | Maruyama et al. |
| 6,395,762 B1 | 5/2002 | Fobare et al. |
| 6,410,734 B1 | 6/2002 | Hu |
| 2002/0022605 A1 | 2/2002 | Sum et al. |
| 2002/0022638 A1 | 2/2002 | Ashwell et al. |
| 2002/0022641 A1 | 2/2002 | Fobare et al. |
| 2002/0028797 A1 | 3/2002 | Sum et al. |
| 2002/0028832 A1 | 3/2002 | Ashwell et al. |
| 2002/0028835 A1 | 3/2002 | Hu et al. |
| 2002/0037907 A1 | 3/2002 | Steffan et al. |
| 2002/0040023 A1 | 4/2002 | Quagliato et al. |
| 2002/0068751 A1 | 6/2002 | Coghlan et al. |

FOREIGN PATENT DOCUMENTS

| | | |
|---|---|---|
| EP | 0 089 154 A2 | 9/1983 |
| EP | 0 236 624 A2 | 9/1987 |
| EP | 0 449 261 A1 | 10/1991 |
| EP | 0 590 793 A1 | 4/1994 |
| EP | 0 659 737 A2 | 6/1995 |
| EP | 0 714 883 A1 | 6/1996 |
| EP | 0 764 640 A1 | 3/1997 |
| EP | 0 801 060 A1 | 10/1997 |
| FR | 2 798 126 A1 | 3/2001 |
| GB | 2 163 150 A | 2/1986 |
| WO | WO 95/29159 A1 | 11/1995 |
| WO | WO 97/41120 A1 | 11/1997 |
| WO | WO 97/46556 A1 | 12/1997 |
| WO | WO 98/22480 A1 | 5/1998 |
| WO | WO 98/32753 A1 | 7/1998 |
| WO | WO 99/65895 | 12/1999 |
| WO | WO 99/65895 A1 | 12/1999 |
| WO | WO 01/17989 A2 | 3/2001 |
| WO | WO 01/43744 A1 | 6/2001 |
| WO | WO 01/44227 A1 | 6/2001 |

Primary Examiner—Joseph K. McKane
Assistant Examiner—Kamal Saeed
(74) Attorney, Agent, or Firm—Kimberly R. Hild

(57) ABSTRACT

This invention provides compounds of Formula I having the structure

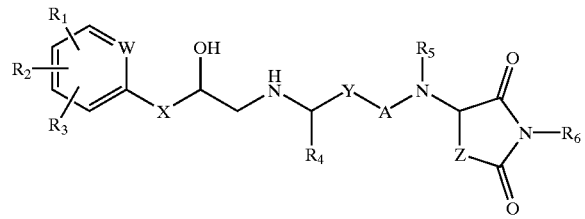

wherein,

A, X, Y, Z, W, $R_1$, $R_2$, $R_3$, $R_4$, $R_5$, and $R_6$ are as defined hereinbefore or a pharmaceutically acceptable salt thereof, which are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension and frequent urination; and are particularly useful in the treatment or inhibition of type II diabetes.

9 Claims, No Drawings

AZOLIDINES AS BETA-3 ADRENERGIC RECEPTOR AGONISTS

This application is a divisional of U.S. Ser. application No. 09/904,161 filed on Jul. 12, 2001 now U.S. Pat. No. 6,465,501 which in turn claims the benefit of U.S. Provisional Application No. 60/218,706, filed on Jul. 17, 2000. The entire disclosure of the Ser. No. 09/904,161 application is hereby incorporated by reference.

BACKGROUND OF THE INVENTION

This invention relates to azolidine derivatives which are $\beta_3$ adrenergic receptor agonists useful for the treatment of metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment of type II diabetes.

The subdivision of β adrenergic receptors (β-AR) into $\beta_1$- and $\beta_2$-AR has led to the development of $\beta_1$- and $\beta_2$-antagonists and/or agonists which have been useful for the treatment of cardiovascular disease and asthma. The recent discovery of "atypical" receptors, later called $\beta_3$-AR, has led to the development of $\beta_3$-AR agonists which may be potentially useful as antiobesity and antidiabetic agents. For recent reviews on $\beta_3$-AR agnoists, see: 1. A. D. Strosberg, Annu. Rev. Pharmacol. Toxicol. 1997, 37, 421; 2. A. E. Weber, Ann. Rep. Med. Chem. 1998, 33,193; 3. C. P. Kordik and A. B. Reitz, J. Med. Chem. 1999, 42, 181; 4. C. Weyer, J. F. Gautier and E. Danforth, Diabetes and Metabolism, 1999, 25, 11.

Compounds that are potent and selective $\beta_3$ agonists, may be potentially useful antiobesity agents. Low levels or lack of $\beta_1$ and $\beta_2$-agonistic properties will minimize or eliminate the adverse side effects that are associated with $\beta_1$ and $\beta_2$ agonistic activities, i.e. increased heart rate, and muscle tremor, respectively.

Early developments in the $\beta_3$-agonist field are described in European patent 427480, U.S. Pat. Nos. 4,396,627, 4,478, 849, 4,999,377, 5,153,210. Although the early developments purport to claim compounds with greater $\beta_3$-AR selectivity over the $\beta_1$- and $\beta_2$-AR. However, clinical trials in humans with those early developed $\beta_3$-agonists have, so far, not been successful.

More recently, potent and selective human $\beta_3$ agonists have been described in several patents and published applications: WO 98/32753, WO 97/46556, WO 97/37646, WO 97/15549, WO 97/25311, WO 96/16938, WO 95/29159, European Patents 659737, 801060, 714883, 764640, 827746, and U.S. Pat. Nos. 5,561,142, 5,705,515, 5,436, 257, and 5,578,620. These compounds were evaluated in Chinese hamster ovary (CHO) cells test procedures, expressing cloned human β3 receptors, which predict the effects that can be expected in humans (Granneman et al., Mol Pharmacol., 1992, 42, 964; Emorine et al., Science, 1989, 245, 1118; Liggett Mol. Pharmacol., 1992, 42, 634).

$\beta_3$-Adrenergic agonists also are useful in controlling the frequent urge of urination. It has been known that relaxation of the bladder detrusor is under beta adrenergic control (Li J H, Yasay G D and Kau S T Pharmacology 1992; 44: 13–18). Beta-adrenoceptor subtypes are in the detrusor of guinea-pig urinary bladder. Recently, a number of laboratories have provided experimental evidence of $\beta_3$ adrenergic receptors in a number of animal species including human (Yamazaki Y, Takeda H, Akahane M, Igawa Y, et al. Br. J. Pharmacol. 1998; 124: 593–599), and that activation of the $\beta_3$ receptor subtype by norepinephrine is responsible for relaxation of the urinary bladder.

Urge urinary incontinence is characterized by abnormal spontaneous bladder contractions that can be unrelated to bladder urine volume. Urge urinary incontinence is often referred to hyperactive or unstable bladder. Several etiologies exist and fall into two major categories, myogenic and neurogenic. The myogenic bladder is usually associated with detrusor hypertrophy secondary to bladder outlet obstruction, or with chronic urinary tract infection. Neurogenic bladders are associated with an uninhibited micturition reflex. An upper motor neuron disease is usually the underlying cause. In either case, the disease is characterized my abnormal spontaneous contractions that result in an abnormal sense of urinary urgency and involuntary urine loss. At present, the most common therapy for hyperactive bladder includes the use of antimuscarinic agents to block the action of the excitatory neurotransmitter acetylcholine. While effective in neurogenic bladders, their utility in myogenic bladders is questionable. In addition, due to severe dry mouth side-effects associated with antimuscarinic therapy, the patient compliance with these agents is only approximately 30%.

In the bladder, $\beta_3$ adrenergic receptor agonists activate adenylyl cyclase and generate cAMP through the G-protein coupled $\beta_3$ receptor. The resulting phosphorylation of phospholamban/calcium ATPase enhances uptake of calcium into the sarcoplasmic reticulum. The decrease in intracellular calcium inhibits bladder smooth muscle contractility.

It is suggested therefore, that activation of the $\beta_3$ adrenergic receptor in the urinary bladder will inhibit abnormal spontaneous bladder contractions and be useful for the treatment of bladder hyperactivity. Note, that unlike the antimuscarinics, $\beta_3$ adrenergic receptor agonists would be expected to be active against both neurogenic and myogenic etiologies.

Despite all these recent developments there is still no single therapy available for the treatment of type II diabetes (NIDDM), obesity, atherosclerosis, gastrointestinal disorders, neurogenetic inflammation, frequent urination and related diseases. A potent and selective $\beta_3$ adrenergic receptor agonist is therefore highly desirable for the potential treatment of such disease states.

DESCRIPTION OF THE INVENTION

This invention provides compounds of Formula I having the structure

I

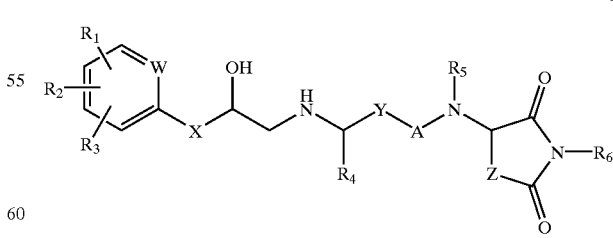

wherein, $R_1, R_2, R_3$ are each, independently, hydrogen, alkyl of 1–6 carbon atoms, aryl of 6 to 10 carbon atoms, aryloxy of 6–10 carbon atoms, halogen, trifluoromethyl of atoms, alkoxy of 1–6 carbon atoms, hydroxy, nitro, amino, aminocarbonyl, alkylamino of 1–6 carbon atoms, dialkyl amino of 1–6 carbon atoms per alkyl group, formamido, ureido, acyl of 2–7 carbon atoms, acylamino of 2–7 carbon atoms, amino, alkylsulfonylamino of 1–6 carbon atoms, or arylsulfonylamino of 6 to 10 carbon atoms; or two of $R_1$, $R_2$, and $R_3$ are taken together to form a phenyl ring or a heterocyclic ring which is fused to the ring which contains the $R_1$, $R_2$, or $R_3$ substituents, wherein the heterocyclic ring contains 1–3 heteroatoms selected from N, O, or S;

$R_4$ is hydrogen or alkyl of 1–6 carbon atoms;

$R_5$ is hydrogen, alkyl of 1–6 carbon atoms, aryl of 6–10 carbon atoms, arylalkyl of 7–14 carbon atoms, halogen substituted arylalkyl of 7–14 carbon atoms, arylalkene of 8–16 carbon atoms, arylalkyne of 8–16 carbon atoms, alkoxycarbonyl of 2–7 carbon atoms, aryloxycarbonyl of 7–11 carbon atoms, alkylsulfonyl of 1–6 carbon atoms, or arylsulfonyl of 1–6 carbon atoms;

$R_6$ is hydrogen, alkyl of 1–6 carbon atoms, aryl or arylalkyl of 7–14 carbon atoms;

A is phenyl, naphthyl, benzofuryl, or benzothienyl;

X is bond, —$OCH_2$—, or —$SCH_2$—;

Y is alkyl of 1–6 carbon atoms, or alkoxy of 1–6 carbon atoms;

Z is carbon, sulfur, oxygen, or nitrogen;

W is carbon or nitrogen;

or a pharmaceutically acceptable salt thereof, which are selective agonists at human $\beta_3$ adrenergic receptors and are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

Alkyl includes both straight chain as well as branched moieties. Alkenyl and alkynyl include both straight chain as well as branched moities, which contain at least one alkene or alkyne group. By definition alkyl also includes alkyl moieties which are optionally mono- or poly substituted with groups such as halogen, hydroxy, cyano, alkoxy, aryloxy, arylalkyl, alkylthio, arylthio, amino, alkylamino, and dialkylamino. Halogen means bromine, chlorine, fluorine, and iodine. Preferred aryl moieties are phenyl and naphthyl.

As used herein, a heterocyclic ring is a ring containing 1–3 heteroatoms selected from N, O, and S, which may be saturated, unsaturated, or partially unsaturated. It is understood that the heterocyclic ring does not contain heteroatoms in arrangements which would make them inherently unstable. For example, the term heterocyclic ring does not include ring systems containing O—O bonds in the ring backbone. When any two of $R_1$, $R_2$, or $R_3$ are taken together to form a heterocyclic ring, the resulting heterocycle will be fused to a phenyl ring. Either ring of the phenyl fused heterocycle may contain the $R_1$, $R_2$, or $R_3$ substituent which is not part of the ring backbone. Similarly when any two $R_1$, $R_2$, or $R_3$ are taken together to form a phenyl ring, the resulting moiety will be a naphthyl ring. Either ring of the naphthyl moiety may contain the $R_1$, $R_2$, or $R_3$ substituent which is not part of the ring backbone. When two of $R_1$, $R_2$, or $R_3$ are taken together to form a heterocyclic ring, preferred phenyl fused heterocyclic rings include benzimidazolone and carbazole.

The compounds of the present invention contain at least one asymmetric center. Additional asymmetric centers may exist on the molecule depending upon the structure of the substituents on the molecule. The compounds may be prepared as a racemic mixture and can be used as such, or may be resolved into the individual isomers. In addition to covering the racemic compounds, this invention also covers all individual isomers, enantiomers, diasteromers or mixtures thereof, regardless of whether the structural representations of the compounds indicate such stereochemistry.

Preferred compounds of Formula I are those in which $R_1$, $R_2$, $R_3$ are each, independently, hydrogen, alkyl of 1–6 carbon atoms, aryl of 6 to 10 carbon atoms, aryloxy of 6–10 carbon atoms, halogen, arylalkoxy of 7–14 carbon atoms, arylalkyl of 7–14 carbon atoms, alkoxy of 1–6 carbon atoms, hydroxy, or alkylsulfonylamino of 1–6 carbon atoms; or two of $R_1$, $R_2$, and $R_3$ are taken together to form a heterocyclic ring which is fused to the ring which contains the $R_1$, $R_2$, or $R_3$ substituents, wherein the heterocyclic ring contains 1–3 heteroatoms selected from N, O, or S;

$R_4$ is hydrogen or alkyl of 1–6 carbon atoms;

$R_5$ is hydrogen, alkyl of 1–6 carbon atoms, halogen substituted arylalkyl of 7–14 carbon atoms, or arylalkyne of 8–16 carbon atoms;

$R_6$ is hydrogen, or alkyl of 1–6 carbon atoms;

A is phenyl, or benzofuryl;

X is bond, or —$OCH_2$—;

Y is alkyl of 1–6 carbon atoms;

Z is sulfur;

W is carbon or nitrogen;

or a pharmaceutically acceptable salt thereof.

Specifically preferred compounds of this invention are:

a) 5-[4-(2-{[(2S)-2-Hydroxy-3-(4-phenoxyphenoxy)propyl]amino}ethyl)anilino]-1,3-thiazolidine-2,4-dione;

b) 5-{4-[2-({(2S)-3-[4-(Benzyloxy)phenoxy]-2-hydroxypropyl}amino)ethyl]anilino}-3-methyl-1,3-thiazolidine-2,4-dione;

c) 5-[4-(2-{[(2R)-2-(3-Chlorophenyl)-2-hydroxyethyl]amino}ethyl)anilino]-3-methyl-1,3-thiazolidine-2,4-dione;

d) 5-{4-[2-({(2S)-3-[4-(Benzyloxy)phenoxy]-2-hydroxypropyl}amino)ethyl]anilino}-1,3-thiazolidine-2,4-dione;

e) 5-[4-(2-{[(2S)-2-Hydroxy-3-(4-hydroxyphenoxy)propyl]amino}ethyl)anilino]-1,3-thiazolidine-2,4-dione;

f) 5-[4-(2-{[(2R)-2-(3-Chlorophenyl)-2-hydroxy-ethyl]amino}ethyl)anilino]-1,3-thiazolidine-2,4-dione;

g) 5-[4-(2-{[(2R)-2-Hydroxy-2-phenylethyl]amino}ethyl)anilino]-1,3-thiazolidine-2,4-dione;

h) 5-[4-(2-{[(2S)-3-(4-Fluorophenoxy)-2-hydroxypropyl]amino}ethyl)anilino]-1,3-thiazolidine-2,4-dione;

i) 5-[4-(2-{[(2S)-2-Hydroxy-3-phenoxypropyl] amino}ethyl)anilino]-1,3-thiazolidine-2,4-dione;
j) 5-[4-(2-{[(2S)-2-Hydroxy-3-(4-methoxyphenoxy)propyl] amino}ethyl)anilino]-1,3-thiazolidine-2,4-dione;
k) 5-{4-[2-({(2S)-3-[3-(Benzyloxy)phenoxy]-2-hydroxypropyl}amino)ethyl]anilino}-1,3-thiazolidine-2,4-dione;
l) 5-[4-(2-{[(2S)-2-Hydroxy-3-(3-hydroxyphenoxy)propyl] aminolethyl)anilino]-1,3-thiazolidine-2,4-dione;
m) 5-[4-(2-{[(2S)-3-(9H-Carbazol-4-yloxy)-2-hydroxypropyl]amino}ethyl)anilino]-1,3-thiazolidine-2,4-dione;
n) N-{5-[(1S)-2-({4-[(2,4-Dioxo-1,3-thiazolidin-5-yl) amino]phenethyl}amino)-1-hydroxyethyl]-2-hydroxyphenyl}methanesulfonamide;
o) 5-[4-(2-{[(2S)-3-(1-Benzofuran-5-yloxy)-2-hydroxypropyl]amino}ethyl)anilino]-1,3-thiazolidine-2,4-dione;
p) 5-[4-(2-{[(2S)-3-(4-Butoxyphenoxy)-2-hydroxypropyl] amino}ethyl)anilino]-1,3-thiazolidine-2,4-dione;
q) 5-[4-(2-{[(2S)-2-Hydroxy-3-phenoxypropyl] amino}ethyl)(methyl)anilino]-1,3-thiazolidine-2,4-dione.;
r) 5-[4-(2-{[(2R)-2-(3-Chlorophenyl)-2-hydroxyethyl] amino}propyl)anilino]-1,3-thiazolidine-2,4-dione;
s) 5-{4-[2-({(2R)-2-Hydroxy-3-[(2-oxo-2,3-dihydro-1H-benzimidazol-4-yl)oxy]propyl}amino)ethyl]anilino}-1,3-thiazolidine-2,4-dione;
t) 5-{[2-({[(2R)-2-(3-Chlorophenyl)-2-hydroxyethyl] amino}methyl)-1-benzofuran-5-yl]amino}-1,3-thiazolidine-2,4-dione;
u) 5-(4-{2-[(2S)-2-Hydroxy-3-(naphthalen-2-yloxy)-propylamino]-ethyl}-phenylamino)-thiazolidine-2,4-dione;
v) 5-(4-{2-[(2S)-3-(Biphenyl-4-yloxy)-2-hydroxy-propylamino]-ethyl}-phenylamino)-thiazolidine-2,4-dione;
w) 5-(4-{2-[2-Hydroxy-3-(naphthalen-1-yloxy)-propylamino]-ethyl}-phenylamino)-thiazolidine-2,4-dione;
x) 5-(4-{2-[(2S)-3-(Benzo[1,3]dioxol-5-yloxy)-2-hydroxy-propylamino]-ethyl}-phenylamino)-thiazolidine-2,4-dione;
y) 5-(4-{2-[(2S)-3-(4-Benzyloxy-phenoxy)-2-hydroxy-propylamino]-ethyl}-phenylamino)-thiazolidine-2,4-dione;
z) 5-[(4-{2-[(2S)-3-(4-Benzyloxy-phenoxy)-2-hydroxy-propylamino]-ethyl}-phenyl)-(4-bromo-benzyl)-amino]-thiazolidine-2,4-dione;
aa) 5-[(4-{2-[(2S)-3-(4-Benzyloxy-phenoxy)-2-hydroxy-propylamino]-ethyl}-phenyl)-methyl-amino]-thiazolidine-2,4-dione;
bb) 5-[(4-{2-[(2S)-3-(4-Benzyloxy-phenoxy)-2-hydroxy-propylamino]-ethyl}-phenyl)-[3-(4-fluoro-phenyl)-prop-2-ynyl]-amino}-thiazolidine-2,4-dione;
cc) 5-[(4-Bromo-benzyl)-(4-{2-[(2S)-2-hydroxy-3-(4-hydroxy-phenoxy)-propylamino]-ethyl}-phenyl)-amino]-thiazolidine-2,4-dione;
dd) 5-((4-Bromo-benzyl)-{4-[2-((2S)-2-hydroxy-3-phenoxy-propylamino)-ethyl]-phenyl}-amino)-thiazolidine-2,4-dione;
ee) 5-{4-[2-((2S)-2-Hydroxy-2-pyridin-3-yl-ethylamino)-ethyl]-phenylamino}-thiazolidine-2,4-dione; and
ff) 5-{4-[2-((2R)-2-Hydroxy-2-pyridin-3-yl-ethylamino)-ethyl]-phenylamino}-thiazolidine-2,4-dione or a pharmaceutically acceptable salt thereof.

The compounds of this invention were be prepared according to the following schemes from commercially available starting materials or starting materials which can be prepared using literature procedures. These schemes show the preparation of representative compounds of this invention.

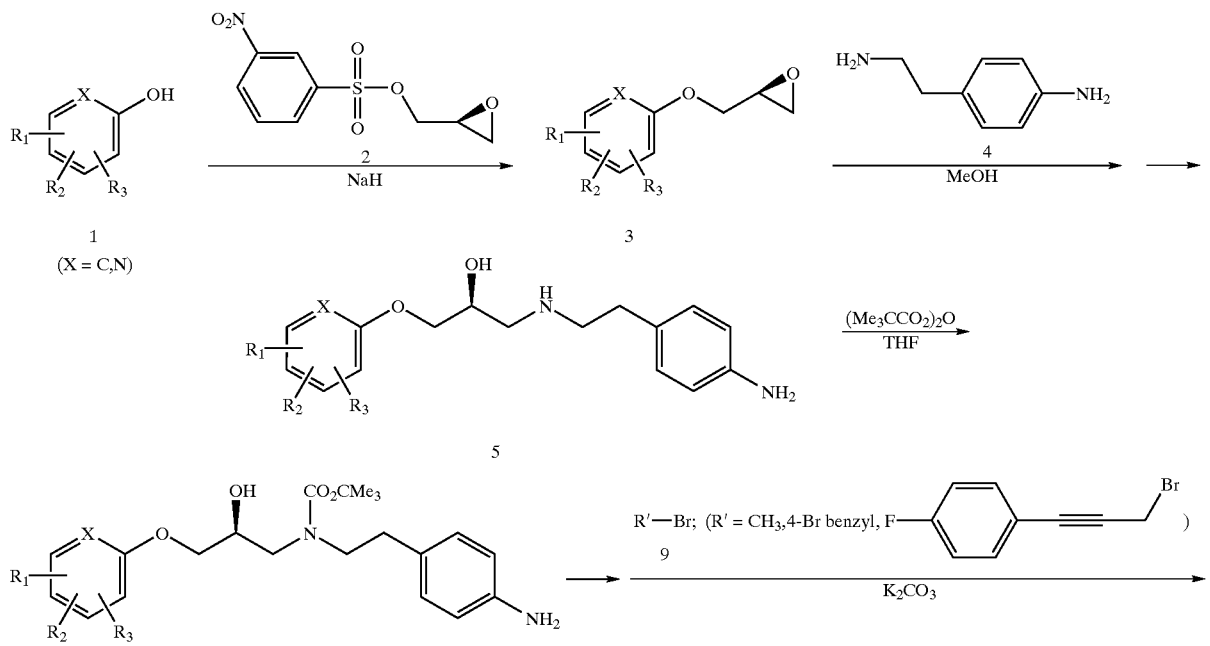

Scheme I

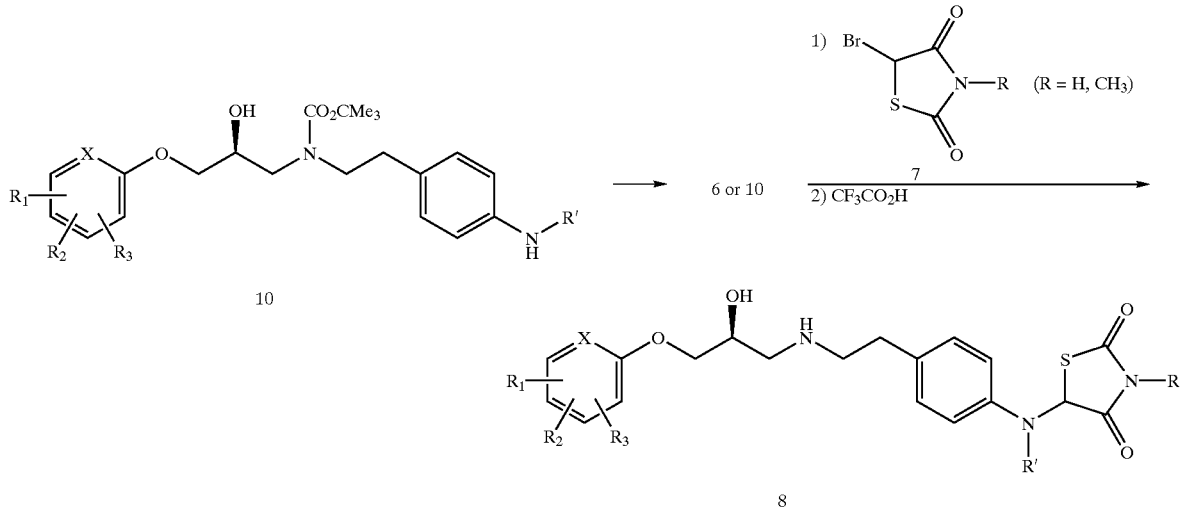

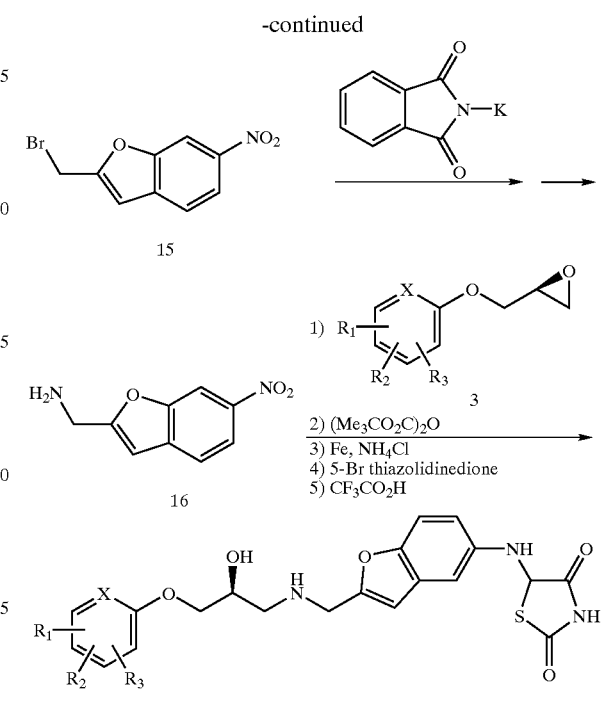

In Scheme I, hydroxyl compounds of structure 1 which are either commercially available or can be prepared by known methods (ref. EP 0764640), can be alkylated with glycidyl benzenesulfonates 2 in the presence of a base, i.e. sodium hydride to produce epoxides 3. Styrene oxides that were used in this invention were commercially available. Refluxing either epoxides 3 or styrene oxides with aniline 4 produced compounds 5. The amino group can be protected selectively using di-tert-butyl dicarbonate at low temperatures (0° C.) to produce carbamates 6. Treatment of the carbamates 6 with bromo-thiazolidinediones 7 in the presence of a base, i.e. triethylamine, in polar solvents, i.e. N,N-dimethylformamide, followed by acidic hydrolysis with either organic or inorganic acids, i.e. trifluoroacetic acid, produced thiazolidinediones 8. The required bromo-thiazolidinediones 7 were prepared according to known methods (ref. *J. Med. Chem.*, 1990, 33 1418–1423). Alkylation of 6 with various alkylating agents 9 in the presence of a base, i.e. potassium carbonate, produced anilines 10. Substituted anilines 10 react with the bromo-thiazolidinediones 7, similarly to anilines 6, to produce alkylated analogues 8.

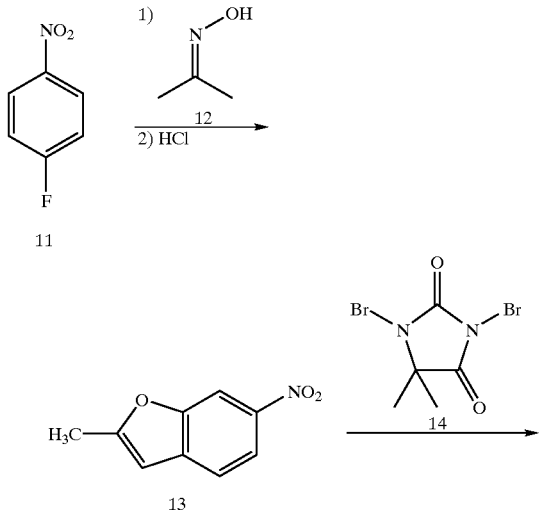

In Scheme II, nitrobenzene 11 was treated with acetoxime in the presence of a base, i.e. sodium hydride, followed by treatment with an ethanolic solution of hydrochloric acid to produce benzofuran 13. Bromination of 13 with 1,3-dibromo-5,5-dimethylhydantoin under UV light gave bromide 15. Conversion of 13 to amine 16 was accomplished in two steps, first alkylation with potassium phthalimide in acetonitrile in the presence crown ether (18-C-6), followed by hydrolysis with hydrazine/ethanol. Amine 16 was converted to the thiazolidinedione 17, in substantially the same manner as in Scheme I.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following standard pharmacological test procedures, which measured the binding selectivity to the $\beta_1$, $\beta_2$, and $\beta_3$ adrenergic receptors. Binding to the receptors was measured in Chinese Hamster ovary (CHO) cells that were transfected with adrenergic receptors. The following briefly summarizes the procedures used and results obtained.

Transfection of CHO cells with $\beta_1$ and $\beta_2$ adrenergic receptors: CHO cells were transfected with human $\beta_1$- or $\beta_2$-adrenergic receptors as described in Tate, K. M., *Eur. J. Biochem.*, 196:357–361 (1991).

Cloning of Human $\beta_3$-AR Genomic DNA: cDNA was constructed by ligating four polymerase chain reaction (PCR) products using the following primers: an ATG-NarI fragment, sense primer 5'-CTTCCCTACCGCCCCACGCG CGATC3' and anti-sense primer 5'CTGGCGCCCAACG GCCAGTGGCCAGTC3'; a NarI-AccI fragment, 5'TTGGC GCTGATGGCCACTGGCCGTTTG3' as sense and 5'GC GCGTAGACGAAGAGCATCACGAG3' as anti-sense primer; an AccI-StyI fragment, sense primer 5'CTCGTGAT GCTCTTCGTCTCACGCGC3' and anti-sense primer 5'GTGAAGGTGCCCATGATGAGACCCAAGG3' and a StyI-TAG fragment, with sense primer 5'CCCTGTGCAC-CTTGGGTCTCATCATGG3' and anti-sense primer 5'CCTCTGCCCCGGTTACCTACCC3'. The corresponding primer sequences are described in Mantzoros, C. S., et.al., *Diabetes* 45: 909–914 (1996). The four fragments are ligated into a pUC 18 plasmid (Gibco-BRL) and sequenced. Full length $\beta_3$ AR clones (402 amino acids) containing the last 6 amino acids of h$\beta_3$ AR are prepared with the $\beta_3$-PARpcDNA3 from ATTC.

Binding Procedure: Clones expressing receptor levels of 70 to 110 fmoles/mg protein were used in the test procedures. CHO cells were grown in 24-well tissue culture plates in Dulbecco's Modified Eagle Media with 10% fetal bovine serum, MEM non-essential amino acids, Penicillin-Streptompycin and Geneticin. On the day of test procedure, growth medium was replaced with preincubation media (Dulbecco's Modified Eagle Media and incubated for 30 minutes at 37° C. Preincubation medium was replaced with 0.2 ml treatment medium containing DMEM media containing 250 $\mu$M IBMX (isobutyl-1-methylxantine) plus 1 mM ascorbic acid with test compound dissolved in DMSO. Test compounds were tested over a concentration range of $10^{-9}$ M to $10^{-5}$ M for $\beta_3$ cells and $10^{-8}$ to $10^{-4}$ M for $\beta_1$ and $\beta_2$ transfected cells. Isoproterenol ($10^{-5}$ M) was used as an internal standard for comparison of activity. Cells were incubated at 37° C. on a rocker for 30 min with the $\beta_3$ cells and 15 min for $\beta_1$ and $\beta_2$ cells. Incubation was stopped with the addition of 0.2N HCl and neutralized with 2.5N NaOH. The plates, containing the cells and neutralized media, were stored at −20 degrees celsius until ready to test for cAMP using the SPA test kit (Amersham).

Data Analysis and Results: Data collected from the SPA test procedure were analyzed as per cent of the maximal isoproterenol response at $10^{-5}$ M. Activity curves were plotted using the SAS statistical and graphics software. $EC_{50}$ values were generated for each compound and the maximal response (IA) developed for each compound is compared to the maximal response of isoproternol at $10^{-5}$ M from the following formula:

$$IA = \frac{\%\ \text{activity compound}}{\%\ \text{activity isoproterenol}}$$

Table I shows the $\beta_3$-adronergic receptor $EC_{50}$ and IA values for the representative compounds of this invention that were evaluated in this standard pharmacological test procedure. These results show that compounds of the present invention have activity at the $\beta_3$-adrenergic receptor. The compounds of this invention had weaker or no activity at $\beta_1$ and/or $\beta_2$-adrenergic receptor.

TABLE I

| Compound No. | $EC_{50}(\beta_3,\ nM)$ | $IA(\beta_3)$ |
|---|---|---|
| Example 4 | 1 | 85 |
| Example 5 | 20 | 99 |
| Example 6 | 7 | 83 |
| Example 7 | 83 | 94 |
| Example 8 | 14 | 66 |
| Example 9 | 0.9 | 98 |
| Example 12 | 3 | 117 |
| Example 13 | 12 | 104 |
| Example 14 | 9 | 111 |
| Example 17 | 17 | 68 |
| Example 18 | 9 | 89 |
| Example 19 | 20 | 71 |
| Example 29 | 3 | 109 |
| Example 31 | 96 | 88 |

Based on the results obtained in these standard pharmacological test procedures, representative compounds of this invention have been shown to be selective $\beta_3$ adrenergic receptor agonists and are therefore useful in treating metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes, and in modulating glucose levels in disorders such as type I diabetes. As used herein, the term modulating means maintaining glucose levels within clinically normal ranges.

As used in accordance with this invention, the term providing an effective amount means either directly administering such a compound of this invention, or administering a prodrug, derivative, or analog which will form an effective amount of the compound of this invention within the body.

It is understood that the effective dosage of the active compounds of this invention may vary depending upon the particular compound utilized, the mode of administration, the condition, and severity thereof, of the condition being treated, as well as the various physical factors related to the individual being treated. As used in accordance with invention, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg. It is preferred that the administration of one or more of the compounds herein begin at a low dose and be increased until the desired effects are achieved.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, , xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, and cattle are generally prepared by mixing the compounds of the present invention with a sufficient amount of animal feed to provide from about 1 to 1000 ppm of the compound in the feed. Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. The supplement is used as a top dressing for the feed, it likewise helps to ensure uniformity of distribution of the active material across the top of the dressed feed.

The preferred medicated swine, cattle, sheep and goat feed generally contain from 0.01 to 400 grams of active ingredient per ton of feed, the optimum amount for these animals usually being about 50 to 300 grams per ton of feed. The preferred poultry and domestic pet feed usually contain about 0.01 to 400 grams and preferably 10 to 400 grams of active ingredient per ton of feed.

For parenteral administration the compounds of the present invention may be prepared in the form of a paste or a pellet and administered as an implant, usually under the skin of the head or ear of the animal in which increase in lean meat deposition and improvement in lean mean to fat ratio is sought. In general, parenteral administration involves injection of a sufficient amount of the compounds of the present invention to provide the animal with 0.001 to 100 mg/kg/day of body weight of the active ingredient. The preferred dosage for swine, cattle, sheep and goats is in the range of from 0.001 to 50 mg/kg/day of body weight of active ingredient; whereas, the preferred dose level for poultry and domestic pets is usually in the range of from 0.001 to 35 mg/kg/day of body weight.

Paste formulations can be prepared by dispersing the active compounds in a pharmaceutically acceptable oil such as peanut oil, sesame oil, corn oil or the like. Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process. It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body. For the poultry and swine raisers, using the method of the present invention yields leaner animals.

Additionally, the compounds of this invention are useful in increasing the lean mass to fat ratio in domestic pets, for the pet owner or veterinarian who wishes to increase leanness and trim unwanted fat from pet animals, the present invention provides the means by which this can be accomplished.

The following procedures describe the preparation of representative examples of this invention.

EXAMPLE 1

5-[4-(2-{[(2S)-2-Hydroxy-3-(4-phenoxyphenoxy)propyl]amino}ethyl)anilino]-1,3-thiazolidine-2,4-dione Step a) (2S)-2-[(4-Phenoxyphenoxy)methyl]oxirane Sodium hydride (60% in mineral oil, 1.08 g, 26.9 mmol) was added portionwise into a cold (0° C.) mixture of 4-phenoxyphenol (5.0 g, 26.9 mmol) and N,N-dimethylformamide (50 mL). The mixture was stirred for 1 hour and then (2S)-oxiranylmethyl 3-nitrobenzenesulfonate (7.67 g, 29.6 mmol) in N,N-dimethylformamide (10 mL) was added dropwise. The new mixture was stirred at room temperature for 18 hours, poured into water and extracted with ethyl acetate. The organic extracts were dried over $MgSO_4$. Evaporation and purification by flash chromatography (hexanes/ethyl acetate 5/1) gave a clear oil (6.2 g, 95% yield): MS m/e 242 $M^+$.

Step b) (2S)-1-[(4-Aminophenethyl)amino]-3-(4-phenoxyphenoxy)-2-propanol

A mixture of (2S)-2-[(4-phenoxyphenoxy)methyl]oxirane (6.0 g, 24.8 mmol), 4-(2-aminoethyl)aniline (10.1 g, 74.4 mmol), and methyl alcohol (100 mL) was refluxed for 5 hours. The volatiles were removed in vacuo and the residue was purified by flash chromatography (hexanes/ethyl acetate/methyl alcohol 1/1/1) to give a white solid (6.6 g, 70% yield): MS m/e 379 $(M+H)^+$;

Analysis for: $C_{23}H_{26}N_2O_3$ Calc'd: C, 72.99; H, 6.93; N, 7.40. Found: C, 72.41; H, 6.93; N, 7.33.

Step c) tert-Butyl 4-aminophenethyl[(2S)-2-hydroxy-3-(4-phenoxyphenoxy)propyl]carbamate Di-tert-butyl dicarbonate (2.88 g, 13.2 mmol) was added into a cold (0° C.) mixture of (2S)-1-[(4-aminophenethyl)amino]-3-(4-phenoxyphenoxy)-2-propanol (5.0 g, 13.2 mmol), and tetrahydrofuran (20 mL). The mixture was stirred at 0° C. for 2 hours, poured into water, and extracted with ethyl acetate. The organic extracts were dried over $MgSO_4$. Evaporation and purification by flash chromatography (hexanes/ethyl acetate 1/1) gave a yellow oil (5.96 g, 95% yield): MS m/e 479 $(M+H)^+$;

Analysis for: $C_{28}H_{24}N_2O_5$ Calc'd: C, 70.27; H, 7.16; N, 5.85. Found: C, 70.14; H, 6.88; N, 5.73.

Step d) tert-Butyl 4-[(2,4-dioxo-1,3-thiazolidin-5-yl)amino]phenethyl[(2S)-2-hydroxy-3-(4-phenoxyphenoxy)propyl]carbamate Triethylamine (1.53, 10.97 mmol) was added into a mixture of tert-butyl 4-aminophenethyl[(2S)-2-hydroxy-3-(4-phenoxyphenoxy)propyl]carbamate (5.2 g, 10.97 mmol), 5-bromo-1,3-thiazolidine-2,4-dione (2.15 g, 10.97 mmol), and N,N-dimethylformamide (50 mL). The mixture was stirred at room temperature for 2 hours, poured into aqueous ammonium chloride and extracted with ethyl acetate. The organic extracts were dried over $MgSO_4$. Evaporation and purification by flash chromatography (hexanes/ethyl acetate 1/1) gave an off-white solid (5.1 g, 78% yield): MS m/e 594 $(M+H)^+$;

Analysis for: $C_{31}H_{35}N_3O_5S$ Calc'd: C, 62.72; H, 5.94; N, 7.08. Found: C, 62.07; H, 5.93; N, 7.02.

Step e) 5-[4-(2-{[(2S)-2-Hydroxy-3-(4-phenoxyphenoxy)propyl]amino}ethyl)anilino]-1,3-thiazolidine-2,4-dione A mixture of tert-butyl 4-[(2,4-dioxo-1,3-thiazolidin-5-yl)amino]phenethyl[(2S)-2-hydroxy-3-(4-phenoxyphenoxy)propyl]carbamate (1.5 g, 2.53 mmol), trifluoroacetic acid (5 mL) and dichloromethane (50 mL) was stirred at room temperature for 24 hours. The volatiles were removed in vacuo and the residue was triturated with ethyl ether to produce a yellow solid (1.32 g, 72% yield): mp 72–74° C.; MS m/e 494 $(M+H)^+$;

Analysis for: $C_{26}H_{27}N_3O_5S \times 1.6$ $CF_3CO_2H$ Calc'd: C, 51.88; H, 4.23; N, 6.21. Found: C, 51.73; H, 4.39; N, 6.13.

EXAMPLE 2

5-{4-[2-({(2S)-3-[4-(Benzyloxy)phenoxy]-2-hydroxypropyl}amino)ethyl]anilino}-3-methyl-1,3-thiazolidine-2,4-dione Step a) tert-Butyl 4-aminophenethyl{(2S)-3-[4-(benzyloxy)phenoxy]-2-hydroxypropyl}carbamate Di-tert-butyl dicarbonate (1.2 g, 5.53 mmol) was added into a cold (0° C.) mixture of (2S)-1-[(4-aminophenethyl)amino]-3-[4-(benzyloxy)phenoxy]-2-propanol (2.17 g, 5.53 mmol), and tetrahydrofuran (20 mL). The mixture was stirred at 0° C. for 2 hours, poured into water, and extracted with ethyl acetate. The organic extracts were dried over $MgSO_4$. Evaporation and purification by flash chromatography (hexanes/ethyl acetate 1/1) gave a yellow oil (2.4 g, 88% yield): MS m/e 493 $(M+H)^+$;

Step b) 3-Methyl-1,3-thiazolidine-2,4-dione

A mixture of N-methylthiourea (45 g, 0.5 mol), chloroacetic acid (47 g, 0.5 mol) and water (250 mL) was refluxed for 48 hours. The mixture was cooled to room temperature and extracted with chloroform. The organic extracts were dried over $MgSO_4$. Evaporation and purification by flash chromatography (hexanes/ethyl acetate 1/2) gave an off-white solid (51.6 g, 79% yield): mp 39–41° C.; MS m/e 131 $M^+$;

Analysis for: $C_4H_5NO_2S$ Calc'd: C, 36.63; H, 3.84; N, 10.68. Found: C, 36.68; H, 3.46; N, 10.44.

Step c) 5-Bromo-3-methyl-1,3-thiazolidine-2,4-dione

Bromine (2.16 mL, 42 mmol) was added dropwise into a cold (0° C.) solution of 3-methyl-1,3-thiazolidine-2,4-dione (5.5 g, 42 mmol), and acetic acid (100 mL). The mixture was allowed to come to room temperature, and then warmed to 60° C. and stirred for 18 hours. The mixture was then poured into water and extracted with ethyl acetate. The organic layer was washed with sodium bisulfite and brine. The organic extracts were dried over $MgSO_4$. Evaporation and purification by flash chromatography (hexanes/ethyl acetate 1/3) gave a clear oil (7.2 g, 82% yield): MS m/e 209 $M^+$;

Analysis for: $C_4H_4BrNO_2S$ Calc'd: C, 22.87; H, 1.92; N, 6.67. Found: C, 22.49; H, 1.69; N, 6.52.

Step d) 5-{4-[2-({(2S)-3-[4-(Benzyloxy)phenoxy]-2-hydroxypropyl}amino)ethyl]anilino}-3-methyl-1,3-thiazolidine-2,4-dione A mixture of tert-butyl 4-aminophenethyl{(2S)-3-[4-(benzyloxy)phenoxy]-2-hydroxypropyl}carbamate (1.2 g, 2.44 mmol), 5-bromo-3-methyl-1,3-thiazolidine-2,4-dione (0.51 g, 2.44 mmol), and N,N-dimethylformamide (15 mL) was stirred at room temperature for 48 hours. The mixture was then poured into aqueous ammonium chloride and extracted with ethyl acetate. The organic extracts were dried over $MgSO_4$. Evaporation and purification by flash chromatography (hexanes/ethyl acetate 1/1) gave a light yellow solid (0.72 g, 57% yield): mp 165–167; MS m/e 520 $(M-H)^+$;

Analysis for: $C_{28}H_{31}N_3O_5S \times 1$ HBr Calc'd: C, 55.91; H, 5.32; N, 6.98. Found: C, 56.86; H, 5.28; N, 7.30.

EXAMPLE 3

5-[4-(2-{[(2R)-2-(3-Chlorophenyl)-2-hydroxyethyl]amino}ethyl)anilino]-3-methyl-1,3-thiazolidine-2,4-dione Step a) tert-Butyl 4-aminophenethyl[(2R)-2-(3-chlorophenyl)-2-hydroxyethyl]carbamate Di-tert-butyl dicarbonate (4.95 g, 22.72 mmol) was added into a cold (0° C.) mixture of (1R)-2-[(4-aminophenethyl)amino]-1-(3-chlorophenyl)-1-ethanol (6.6 g, 22.72 mmol), and tetrahydrofuran (30 mL). The mixture was stirred at 0°

C. for 2 hours, poured into water, and extracted with ethyl acetate. The organic extracts were dried over MgSO$_4$. Evaporation and purification by flash chromatography (ethyl acetate/methyl alcohol 5/1) gave a yellow oil (7.4 g, 83% yield): MS m/e 390 M$^+$;

Analysis for: C$_{21}$H$_{27}$ClN$_2$O$_3$ Calc'd: C, 64.52; H, 6.96; N, 7.17. Found: C, 63.49; H, 6.49; N, 6.71.

Step b) 5-[4-(2-{[(2R)-2-(3-Chlorophenyl)-2-hydroxyethyl] amino}ethyl)anilino]-3-methyl-1,3-thiazolidine-2,4-dione A mixture of tert-butyl 4-aminophenethyl[(2R)-2-(3-chlorophenyl)-2-hydroxyethyl]carbamate (1.9 g, 4.85 mmol), 5-bromo-3-methyl-1,3-thiazolidine-2,4-dione (1.02 g, 4.85 mmol), and N,N-dimethylformamide (15 mL) was stirred at 60° C. for 24 hours. The mixture was then poured into aqueous ammonium chloride and extracted with ethyl acetate. The organic extracts were dried over MgSO$_4$. Evaporation and purification by flash chromatography (ethyl acetate/methyl alcohol 20/1) gave an oil (1.82 g) which was taken in dichloromethane (50 mL) and treated with trifluoroacetic acid (5 mL) for 36 hours. The volatiles were then removed in vacuo and the residue was purified by flash chromatography (ethyl acetate/methyl alcohol 10/1) to give a light yellow solid (1.2 g, 60% yield): mp 129–131; MS m/e 420 (M+H)$^+$;

Analysis for: C$_{20}$H$_{22}$ClN$_3$O$_3$S Calc'd: C, 57.20; H, 5.28; N, 10.01. Found: C, 56.99; H, 5.30; N, 9.58.

EXAMPLE 4

5-{4-[2-({(2S)-3-[4-(Benzyloxy)phenoxy]-2-hydroxypropyl}amino)ethyl]anilino}-1,3-thiazolidine-2,4-dione Step a) (2S)-2-{[4-(Benzyloxy)phenoxy]methyl}oxirane Sodium hydride (60% in mineral oil, 2.2 g, 54.0 mmol) was added portionwise into a cold (0° C.) mixture of 4-(benzyloxyphenol 9.26 g, 46.29 mmol) and N,N-dimethylformamide (25 mL). The mixture was stirred for 1 hour and then (2S)-(+)-oxiranylmethyl 3-nitrobenzenesulfonate (10 g, 38.5 mmol) in N,N-dimethylformamide (25 mL) was added dropwise. The new mixture was warmed up to room temperature, stirred for 18 hours, poured into water, and extracted with ethyl acetate. The organic extracts were washed with brine, and dried over MgSO$_4$. Evaporation and purification by flash chromatography (hexanes/ethyl acetate 9/1) gave a white solid (6.2 g, 62% yield), MS m/e 256 (M)$^+$; $^1$H NMR (DMSO-d$_6$ 300 MHz) 67 2.68 (m, 1H), 3.28 (m, 1H), 3.74 (m, 1H), 4.21 (m, 1H), 5.02 (s, 2H), 6.91 (m, 4H), 7.40 (m, 5H);

Analysis for C$_{16}$H$_{16}$N$_4$O$_3$ Calc'd: C, 74.98; H, 6.29. Found: C, 74.46, H, 6.32.

Step b) (2S)-1-[(4-Aminophenethyl)amino]-3-[4-(benzyloxy)phenoxy]-2-propanol

This compound was prepared from (2S)-2-{[4-(benzyloxy)phenoxy]methyl}oxirane and 4-(2-aminoethyl) aniline as described in example 1, step b, with one modification, the mixture was stirred in tetrahydrofuran and the product was triturated with ethyl ether to give a white solid (47% yield): MS m/e 393 (M+H)$^+$; $^1$H NMR (DMSO-d$_6$ 300 MHz) δ1.61 (br 2H), 2.75 (m, 3H), 2.85 (m, 3H), 3.56 (s, 2H), 3.97 (m, 2H), 3.99 (m, 1H), 5.01 (s, 2H), 6.63 (m, 2H), 6.81 (m, 2H), 6.82 (m, 2H), 6.83 (m, 2H), 7.37 (m, 5H);

Analysis for C$_{24}$H$_{28}$N$_2$O$_3$ Calc'd: C, 73.44; H, 7.19; N, 7.14. Found: C, 73.02; H, 7.15; N, 6.86.

Step c) tert-Butyl 4-aminophenethyl{(2S)-3-[4-(benzyloxy) phenoxy]-2-hydroxypropyl}carbamate This compound was prepared from (2S)-1-[(4-aminophenethyl)amino]-3-[4-(benzyloxy)phenoxy]-2-propanol and di-tert-butyl dicarbonate in substantially the same manner as described in example 1, step c, and was obtained as colorless oil (85% yield ), MS m/e 492 (M)$^+$; $^1$H NMR (DMSO-d$_6$ 300 MHz) δ1.45 (s, 9H), 2.71 (m, 2H), 3.41 (m, 4H), 3.44 (m, 2H), 3.86 (m, 2H), 4.11 (m, 2H), 5.01 (s, 2H), 6.62 (d, 2H), 6.83 (d, 2H), 6.91 (m, 4H), 7.37 (m, 5H).

Step d) tert-Butyl (2S)-3-[4-(benzyloxy)phenoxy]-2-hydroxypropyl{4-[(2,4-dioxo-1,3-thiazolidin-5-yl)amino] phenethyl}carbamate This compound was prepared from tert-butyl 4-aminophenethyl{(2S)-3-[4-(benzyloxy)phenoxy]-2-hydroxypropyl}carbamate and 5-bromo-1,3-thiazolidine-2,4-dione in substantially the same manner as described in example 1, step d, and was obtained as yellow foam solid (66% yield): MS m/e 607 (M)$^+$; $^1$H NMR (DMSO-d$_6$ 300 MHz) δ1.44 (s, 9H), 1.70 (br, 1H), 2.79 (m, 2H), 3.44 (m, 4H), 3.82 (m, 2H), 4.08 (m, 1H), 4.58 (d, 1H), 5.01 (s, 2H), 6.07 (d, 1H), 6.61 (d, 2H), 6.91 (m, 2H), 7.08 (m, 2H), 7.41 (m, 5H), 8.8 (br, 1 H).

Step e) 5-{4-[2-({(2S)-3-[4-(Benzyloxy)phenoxy]-2-hydroxypropyl}amino)ethyl]anilino}-1,3-thiazolidine-2,4-dione This compound was prepared from tert-butyl (2S)-3-[4-(benzyloxy)phenoxy]-2-hydroxypropyl{4-[(2,4-dioxo-1,3-thiazolidin-5-yl)amino]phenethyl}carbamate and trifluoroacetic acid in substantially the same manner as described in example 1, step e, with one modification, the product was isolated as the free base and recrystallized from methanol, tetrahydrofuran, hexanes to give a yellow foam solid (58% yield): mp 152° C.; MS m/e 508 (M+H)$^+$; $^1$H NMR (DMSO-d$_6$ 300 MHz) δ2.68 (m, 2H), 2.81 (m, 1H), 2.88 (m, 4H), 3.85 (m, 2H), 4.00 (m, 1H), 5.02 (s, 2H), 5.45 (br, 1H), 5.99 (d, 1H), 6.59 (d, 2H), 6.66 (d, 1H), 6.84 (d, 2H), 6.86 (m, 2H) 6.92 (m, 2H), 7.28 (m, 5H), 8.80 (br, 1 H);

Analysis for C$_{27}$H29N$_3$O$_5$Calc'd: C, 63.89; H, 5.76; N, 8.28. Found: C, 63.91; H, 5.90; N, 7.93.

EXAMPLE 5

5-[4-(2-{[(2S)-2-Hydroxy-3-(4-hydroxyphenoxy)propyl] amino}ethyl)anilino]-1,3-thiazolidine-2,4-dione Step a) tert-Butyl 4-aminophenethyl[(2S)-2-hydroxy-3-(4-hydroxyphenoxy)propyl]carbamate A mixture of tert-butyl 4-aminophenethyl{(2S)-3-[4-(benzyloxy)phenoxy]-2-hydroxypropyl}carbamate (1.2 g, 2.53 mmol), 10% Pd/C (0.1 g), and ethanol (30 mL) was hydrogenated on a Parr Shaker at 40 psi for 20 hours. The catalyst was removed by filtration through celite. Evaporation and purification by flash chromatography (hexanes/ ethyl acetate/methanol 6/3/1) gave a white foam solid (0.79 g, 78% yield): MS m/s 403 (M+H)$^+$; $^1$H NMR (CDCl$_3$ 300 MHz) δ1.45 (s, 9H), 2.73 (m, 2H), 3.41 (m, 4H), 3.58 (m, 2H), 3.86 (m, 2H), 4.09 (m, 2H), 4.95 (br, 1H), 6.60 (d, 2H), 6.75 (m, 4H), 6.93 (d, 2H).

Step b) tert-Butyl 4-[(2,4-dioxo-1,3-thiazolidin-5-yl)amino] phenethyl[(2S)-2-hydroxy-3-(4-hydroxyphenoxy)propyl] carbamate This compound was prepared from tert-butyl 4-aminophenethyl[(2S)-2-hydroxy-3-(4-hydroxyphenoxy) propyl]carbamate and 5-bromo-1,3-thiazolidine-2,4-dione in substantially the same manner as described in example 1, step d, with one change, the compound was purified by flash chromatography (hexanes/ethyl acetate/methanol 5/4/1) and was obtained as a light yellow solid (89% yield): MS m/e 518 (M+H)$^+$; $^1$H NMR (DMSO-d$_6$ 300 MHz) δ1.97 (s, 9H), 3.27 (m, 1H), 3.31 (m, 5H), 3.70 (m, 2H), 3.89 (m, 1H), 5.05 (m, 1H), 6.48 (d, 1H), 6.63 (d, 2H), 6.64 (d, 2H), 6.70 (d, 2H), 6.95 (m, 3H), 8.87(s, 1H), 12.16 (s, 1H).

Step c) 5-[4-(2-{[(2S)-2-Hydroxy-3-(4-hydroxyphenoxy) propyl]amino}ethyl)anilino]-1,3-thiazolidine-2,4-dione This compound was prepared from tert-butyl 4-[(2,4-dioxo-1,3-thiazolidin-5-yl)amino]phenethyl[(2S)-2-hydroxy-3-(4-hydroxyphenoxy)propyl]carbamate and trifluoroacetic acid as described in example 1, step e, with modification, the product was isolated as the free base, extracted from the aqueous layer with n-butanol and purified by flash chromatography (hexanes/ethyl acetate/methanol 4/3/3) to give a white solid (20% yield): mp 165° C.; MS m/e 418 (M+H)$^+$; $^1$H NMR (DMSO-d$_6$ 300 MHz) δ2.68 (m, 2H), 2.71 (m, 1H), 2.97 (m, 3H), 3.79 (d, 2H), 3.98 (m, 1H), 5.95 (d, 1H), 6.58 (d, 2H), 6.64 (m, 1H), 6.64 (d, 2H), 6.67 (d, 1H), 6.97 (d, 2H), 8.94 (br, 1H), other $^1$H exchangeable are broad;

Analysis for C$_{20}$H$_{23}$N$_3$O$_5$Calc'd: C, 57.54; H, 5.55; N, 10.07. Found: C, 57.25; H, 5.41; N, 9.82.

EXAMPLE 6

5-[4-(2-{[(2R)-2-(3-Chlorophenyl)-2-hydroxy-ethyl] amino}ethyl)anilino]-1,3-thiazolidine-2,4-dione Step a) (1R)-2-[(4-Aminophenethyl)amino]-1-(3-chlorophenyl)-1-ethanol This compound was prepared from (S)-3-chlorostyrene oxide and 4-(2-aminoethyl)aniline as described in example 1, step b, with modification, the mixture was stirred in tetrahydrofuran. The solvent was removed and the product was triturated in ethyl ether to give a white solid (33% yield): MS m/e 291 (M+H)$^+$; $^1$H NMR (DMSO-d$_6$ 300 MHz) δ2.65 (m 3H), 2.69 (m, 3H), 4.62 (d, 1H), 6.64 (d, 2H), 6.99 (d, 2H), 7.26 (m, 3H), 7.36 (s, 1H), all $^1$H exchangeable are broad;

Analysis for C$_{16}$H$_{19}$ClN$_2$O Calc'd: C, 66.09; H, 6.59; N, 9.63. Found: C, 66.35; H, 6.73; N, 9.80.

Step b) tert-Butyl 4-aminophenethyl[(2R)-2-(3-chlorophenyl)-2-hydroxyethyl]carbamate This compound was prepared from (1R)-2-[(4-aminophenethyl)amino]-1-(3-chlorophenyl)-1-ethanol and di-tert-butyl dicarbonate in substantially the same manner as described in example 1, step c, and was obtained as a colorless oil (78% yield): MS m/e 391 (M+H)$^+$; $^1$H NMR (CDCl$_3$ 300 MHz) δ1.47 (s, 9H), 2.63 (br, 2H), 3.16 (br, 1H), 3.27 (d, 1H), 3.41 (br, 1H), 3.57 (s, 2H), 4.64 (br, 1H), 4.82 (br, 1H), 6.62 (d, 2H), 6.91 (d, 2H), 7.23 (d, 3H), 7.34(d, 1H).

Step c) tert-Butyl (2R)-2-(3-chlorophenyl)-2-hydroxyethyl{4-[(2,4-dioxo-1,3-thiazolidin-5-yl)amino] phenethyl}carbamate This compound was prepared from tert-butyl 4-aminophenethyl[(2R)-2-(3-chlorophenyl)-2-hydroxyethyl]carbamate and 5-bromo-1,3-thiazolidine-2,4-dione in substantially the same manner as described in example 1, step d, and was obtained as a yellow foam solid (59% yield): MS m/e 506 (M+H)$^+$; $^1$H NMR (DMSO-d$_6$ 300 MHz) δ1.31 (d, 9H), 2.59 (m, 2H), 3.25 (m, 4H), 4.72 (br, 1H),5.56 (m, 1H), 6.48 (d, 1H), 6.60 (d, 2H), 7.01(m, 3H), 7.33 (m, 4H), 2.16 (br, 1H).

Step d) 5-[4-(2-{[(2R)-2-(3-Chlorophenyl)-2-hydroxyethyl]amino}ethyl)anilino]-1,3-thiazolidine-2,4-dione This compound was prepared from tert-butyl (2R)-2-(3-chlorophenyl)-2-hydroxyethyl{4-[(2,4-dioxo-1,3-thiazolidin-5-yl)amino]phenethyl}carbamate and trifluoroacetic acid in substantially the same manner as described in example 1, step e, with one modification, the product was isolated as the free base, extracted from the aqueous layer with ethyl acetate and purified by flash chromatography (dichloromethane/methanol/ammonium hydroxide 9/0.99/0.01), and was obtained as a light yellow solid (25% yield): mp 162° C., MS m/e 406 (M+H); $^1$H NMR (DMSO-d$_6$ 300 MHz) δ2.67 (m, 2H), 2.90 (m, 4H), 4.74 (m, 1H), 5.87 (br, H), 6.02 (d, 1H), 6.56 (d, 2H), 6.99 (d, 2H), 7.36 (m, 4H), 7.98 (br, 1H), other exchangeable $^1$H are broad. Analysis for C$_{19}$H$_{20}$ClN$_3$O$_3$S Calc'd: C, 56.22; H, 4.97,; N, 10.35. Found: C, 55.92; H, 4.99; N, 10.19.

EXAMPLE 7

5-[4-(2-{[(2R)-2-Hydroxy-2-phenylethyl]amino}ethyl) anilino]-1,3-thiazolidine-2,4-dione Step a) (1R)-2-[(4-Aminophenethyl)amino]-1-phenyl-1-ethanol This compound was prepared from (S)-styrene oxide and 4-(2-aminoethyl)aniline, as described in example 1, step b, with one modification, the mixture was reflux in tetrahydrofuran. The solvent was removed and the product triturated in ethyl ether to give a white solid (32% yield): MS m/e 257 (M+H)$^+$; $^1$H NMR (DMSO-d$_6$ 300 MHz) δ2.67 (m 3H), 2.89 (m, 3H), 3.57 (br, 2H), 4.65 (m 1H), 6.64 (d, 2H), 6.99 (d, 2H), 7.27 (m, 1H), 7.34 (m, 4H), other $^1$H exchangeable are broad.

Analysis for C$_{16}$H$_{20}$N$_2$O Calc'd: C, 74.97; H, 7.86; N, 10.93. Found: C, 75.01; H, 7.58; N, 10.88.

Step b) tert-Butyl 4-aminophenethyl[(2R)-2-hydroxy-2-phenylethyl]carbamate

This compound was prepared from (1R)-2-[(4-aminophenethyl)amino]-1-phenyl-1-ethanol and di-tert-butyl dicarbonate in substantially the same manner as described in example 1, step c, and was obtained as a colorless oil (88% % yield): MS m/e 356 (M)$^+$; $^1$H NMR (DMSO-d$_6$ 300 MHz) δ1.32 (d, 9H), 2.48 (m, 2H), 3.22 (m, 4H), 4.67 (m, 1H), 4.68 (s, 2H), 5.40 (dd, 1H), 6.46 (d, 2H), 6.77 (m, 2H), 7.29

Step c) tert-Butyl 4-[(2,4-dioxo-1,3-thiazolidin-5-yl)amino] phenethyl[(2R)-2-hydroxy-2-phenylethyl]carbamate This compound was prepared from tert-butyl 4-aminophenethyl[(2R)-2-hydroxy-2-phenylethyl] carbamate and 5-bromo-1,3-thiazolidine-2,4-dione in substantially the same manner as described in example 1, step d, and was obtained as a light yellow solid (25% yield): MS m/e 471 (M)$^+$; $^1$H NMR (DMSO-d$_6$ 300 MHz) δ1.32 (s, 9H), 2.58 (m, 2H), 3.25 (m, 3H), 4.69 (m, 2H), 5.40 (m, 1H), 6.57 (d, 1H), 6.60 6.97 (m, 3H), 7.24 (m, 5H), 12.15 (s, 1H).

Step d) 5-[4-(2-{[(2R)-2-Hydroxy-2-phenylethyl] amino}ethyl)anilino]-1,3-thiazolidine-2,4-dione This compound was prepared from tert-butyl 4-[(2,4-dioxo-1,3-thiazolidin-5-yl)amino]phenethyl[(2R)-2-hydroxy-2-phenylethyl]carbamate and trifluoroacetic acid in substantially the same manner as described in example 1, step e, and was obtained as a yellow solid (52% yield): mp 55° C.; MS m/e 372 (M+H)$^+$; $^1$H NMR (DMSO-d$_6$ 300 MHz) δ2.90 (m, 2H), 3.40 (m, 4H), 3.60 (br, 1H), 4.90 (d, 1H), 6.18 (br, 1H),6.48 (d, 1H), 6.65 (d, 2H), 7.08 (d, 3H), 7.33 (m, 1H), 7.39 (m, 4H), 8.85 (br, 1H),12.21 (br, 1H);

Analysis for C$_{19}$H$_{21}$N$_3$O$_3$S×1.0 CF$_3$CO$_2$H Calc'd: C, 51.90; H, 4.57; N, 8.66. Found: C, 51.21; H, 4.66; N, 8.34.

EXAMPLE 8

5-[4-(2-{[(2S)-3-(4-Fluorophenoxy)-2-hydroxypropyl] amino}ethyl)anilino]-1,3-thiazolidine-2,4-dione Step a) (2S)-2-[(4-Fluorophenoxy)methyl]oxirane This compound was prepared from 4-fluorophenol and (2S)(+)oxiranylmethyl 3-nitrobenzenesulfonate in substantially the same manner as described in example 1, step a, and was obtained as a colorless oil (80% yield): MS m/e 168 M$^+$; $^1$H NMR (DMSO-d$_6$ 300 MHz) δ2.69 (m, 1H), 2.82 (m, 1H), 3.30 (m, 1H), 3.81 (m, 1H), 4.30 (m, 1H), 6.97 (d, 2H), 7.13 (d, 2H).

Step b) (2S)-1-[(4-Aminophenethyl)amino]-3-(4-fluorophenoxy)-2-propanol

This compound was prepared from (2S)-2-[(4-fluorophenoxy)methyl]oxirane and 4-(2-aminoethyl)aniline as described in example 1, step b, with one modification, the mixture was stirred at 70° C. in tetrahydrofuran. The solvent was removed in vacuo and the product was triturated with ethyl ether to give a white solid (51% yield): MS m/e 304 M$^+$; $^1$H NMR (CDCl$_3$ 300 MHz) δ1.22 (br 1H), 2.71 (m, 3H), 2.84 (m, 3H), 3.40 (br, 1H), 3.57 (s, 2H), 3.90 (m, 2H), 3.99 (m, 1H), 6.64 (d, 2H), 6.83 (d, 2H), 6.95 (d, 4H), 6.98 (d, 2H);

Analysis for C$_{17}$H$_{21}$FN$_2$O$_2$Calc'd: C, 67.09; H, 6.96; N, 9.20. Found: C, 66.80; H, 7.02, N, 9.12.

Step c) tert-Butyl 4-aminophenethyl[(2S)-3-(4-fluorophenoxy)-2-hydroxy propyl]carbamate This compound was prepared from (2S)-1-[(4-aminophenethyl)amino]-3-(4-fluorophenoxy)-2-propanol and di-tert-butyl dicarbonate in substantially the same manner as described in example 1, step c, and was obtained as a colorless oil (76% yield): MS m/e 405 (M+H)$^+$; $^1$H NMR (CDCl$_3$ 300 MHz) δ1.45 (s, 9H), 2.71 (m, 2H), 3.41 (m, 4H), 3.57 (m, 2H), 3.82 (m, 1H), 3.84 (m, 1H), 4.07 (m, 2H), 6.62 (d, 2H), 6.82 (d, 2H), 6.94 (m, 4H);

Analysis for C$_{22}$H$_{29}$FN$_2$O$_4$Calc'd: C, 65.33; H, 7.23; N, 6.93. Found: C, 6.93; H, 7.24; N, 6.72.

Step d) tert-Butyl 4-[(2,4-dioxo-1,3-thiazolidin-5-yl)amino]phenethyl[(2S)-3-(4-fluorophenoxy)-2-hydroxypropyl]carbamate This compound was prepared from tert-butyl 4-aminophenethyl[(2S)-3-(4-fluorophenoxy)-2-hydroxypropyl]carbamate and 5-bromo-1,3-thiazolidine-2,4-dione in substantially the same manner as described in example 1, step d, and was obtained as a yellow solid (69% yield): MS m/e 519 (M)$^+$; $^1$H NMR (DMSO-d$_6$ 300 MHz) δ1.28 (s, 9H), 2.85 (br, 1H), 3.08 (br, 1H), 3.31 (m, 4H), 3.78 (m, 2H), 3.82 (m, 1H), 6.40 (s, 1H), 6.59 (d, 2H), 6.88 (d, 2H), 6.97 (d, 2H), 7.04 (d, 2H), all $^1$H exchangeable are broad.

Step e) 5-[4-(2-{[(2S)-3-(4-Fluorophenoxy)-2-hydroxypropyl]amino}ethyl)anilino]-1,3-thiazolidine-2,4-dione This compound was prepared from tert-butyl 4-[(2,4-dioxo-1,3-thiazolidin-5-yl)amino]phenethyl[(2S)-3-(4-fluorophenoxy)-2-hydroxypropyl]carbamate and trifluoroacetic acid in substantially the same manner as described in example 1, step e, and was obtained as a yellow solid (90%): mp 55° C.; MS m/e 420 (M+H)$^+$; $^1$H NMR (DMSO-d$_6$ 300 MHz) δ2.81 (m, 2H), 3.03 (m, 1H), 3.20 (m, 2H), 3.95 (m, 2H), 4.01 (m, 1H), 6.48 (s, 1H), 6.63 (d, 2H), 6.96 (d, 2H), 7.07 (m, 4H), all $^1$H exchangeable are broad.

Analysis for C$_{20}$H$_{22}$FN$_3$O$_4$S×1 CF$_3$COOH×1.39 H$_2$O Calc'd: C, 47.26; H, 4.43; N, 7.52. Found: C, 47.04; H, 4.18; N, 7.02.

EXAMPLE 9

5-[4-(2-{[(2S)-2-Hydroxy-3-phenoxypropyl]amino}ethyl)anilino]-1,3-thiazolidine-2,4-dione Step a) (2S)-2-(Phenoxymethyl)oxirane This compound was prepared from phenol and (2S)(+)oxiranylmethyl 3-nitrobenzenesulfonate in substantially the same manner as described in example 1, step a, and was obtained a colorless oil (73% yield): MS m/e 150 M$^+$; $^1$H NMR (DMSO-d$_6$ 300 MHz) δ2.69 (m, 1H), 2.82 (m, 1H), 3.31 (m, 1H), 3.81 (m, 1H), 4.28 (m, 1H), 6.95 (m, 3H), 7.27 (m, 2H).

Step b) (2S)-1-[(4-Aminophenethyl)amino]-3-phenoxy-2-propanol

This compound was prepared from (2S)-2-(phenoxymethyl)oxirane and 4-(2-aminoethyl)aniline as described in example 1, step b, with one modification, the mixture was stirred at 70° C. in tetrahydrofuran. The solvent was removed in vacuo and the product was triturated with ethyl ether to give a white solid (46% yield): MS m/e 286 M$^+$, $^1$H NMR (CDCl$_3$ 300 MHz) δ1.54 (br, 1H), 2.70 (m, 3H), 2.85 (m, 3H), 3.40 (br, 1H), 3.57 (s, 2H), 3.96 (m, 2H), 4.01 (m, 1H), 6.64 (d, 2H), 6.88 (d, 2H), 6.90 (m, 3H), 7.25 (m, 2H);

Analysis for C$_{17}$H$_{22}$N$_2$O$_2$Calc'd: C, 71.30; H, 7.74; N, 9.78. Found: C, 70.83; H, 7.72; N, 9.83.

Step c) tert-Butyl 4-aminophenethyl[(2S)-2-hydroxy-3-phenoxypropyl]carbamate

This compound was prepared from (2S)-1-[(4-aminophenethyl)amino]-3-phenoxy-2-propanol and di-tert-butyl dicarbonate in substantially the same manner as described in example 1, step c, and was obtained as a colorless oil (84% yield): MS m/e 387 (M+H)$^+$; $^1$H NMR (CDCl$_3$ 300 MHz) δ1.46 (s, 9H), 2.71 (m, 2H), 3.41 (m, 4H), 3.57 (m, 2H), 3.88 (m, 1H), 3.96 (m, 1H), 4.09 (m, 2H), 6.62 (d, 2H), 6.96 (d, 2H), 6.97 (m, 3H), 7.25 (m, 2H);

Analysis for C$_{22}$H$_{30}$N$_2$O$_4$Calc'd: C, 68.37; H, 7.82; N, 7.25. Found: C, 68.08; H, 7.76; N, 6.76.

Step d) tert-Butyl 4-[(2,4-dioxo-1,3-thiazolidin-5-yl)amino]phenethyl[(2S)-2-hydroxy-3-phenoxypropyl]carbamate This compound was prepared from tert-butyl 4-aminophenethyl[(2S)-2-hydroxy-3-phenoxypropyl]carbamate and 5-bromo-1,3-thiazolidine-2,4-dione in substantially the same manner as described in example 1, step d, and was obtained as a yellow solid (69% yield); MS m/e 502 M$^+$; H NMR (DMSO-d$_6$ 300 MHz) δ1.33 (s, 9H), 3.01 (br, 1H), 3.08 (br, 1H), 3.31 (m, 5H), 3.82 (m, 2H), 3.89 (m, 1H), 5.12 (m, 1H), 6.49 (d, 1H), 6.60 (d, 2H), 6.88 (d, 2H), 6.98 (m, 3H), 7.28 (m, 2H),12.16 (s, 1H).

Step e) 5-[4-(2-{[(2S)-2-Hydroxy-3-phenoxypropyl]amino}ethyl)anilino]-1,3-thiazolidine-2,4-dione This compound was prepared from tert-butyl 4-[(2,4-dioxo-1,3-thiazolidin-5-yl)amino]phenethyl[(2S)-2-hydroxy-3-phenoxypropyl]carbamate and trifluoroacetic acid in substantially the same manner as described in example 1, step e, and was obtained as a yellow solid (90% yield): mp 55° C.; MS m/e 420 (M+H)$^+$; $^1$H NMR (DMSO-d$_6$ 300 MHz) δ2.81 (m, 3H), 3.98 (m, 2H), 4.15 (m, 1H), 3.98 (m, 2H), 4.15 (m, 1H), 5.86 (br, 1H) 6.50 (d, 1H), 6.63 (d, 2H), 6.96 (m, 3H), 7.09 (m, 3H), 7.29 (m, 2H), 8.60 (br, 2H), 12.21 (br, 1H);

Analysis for C$_{20}$H$_{23}$N$_3$O$_4$S×1CF$_3$COOH×0.84 H$_2$O Calc'd: C, 49.75; H, 4.83; N, 7.91. Found: C, 49.07; H, 4.38; N, 7.33.

EXAMPLE 10

5-[4-(2-{[(2S)-2-Hydroxy-3-(4-methoxyphenoxy)propyl]amino}ethyl)anilino]-1,3-thiazolidine-2,4-dione Step a) (2S)-2-[(4-Methoxyphenoxy)methyl]oxirane This compound was prepared from 4-methoxyphenol and (2S)(+)oxiranylmethyl 3-nitrobenzenesulfonate in substantially the same manner as described in example 1, step a, and was obtained as a colorless oil (64% yield): MS m/e 180 M$^+$; $^1$H NMR (DMSO-d$_6$ 300 MHz) δ2.78 (m, 1H) 2.85 (m, 1H), 3.38 (m, 1H), 3.71 (m, 3H), 3.80 (m, 1H), 4.25 (m, 1H), 6.98 (m, 4H).

Step b) (2S)-1-[(4-Aminophenethyl)amino]-3-(4-methoxyphenoxy)-2-propanol

This compound was prepared from (2S)-2-[(4-methoxyphenoxy)methyl]oxirane and 4-(2-aminoethyl)

aniline as described in example1, step b, with one modification, the mixture was stirred at 70° C. in tetrahydrofuran. The solvent was removed in vacuo and the product was triturated with ethyl ether to give a white solid (67% yield): mp 60° C., MS m/e 317 (M+H)$^+$; $^1$H NMR (CDCl$_3$ 300 MHz) δ1.60 (br, 2H), 2.75 (m, 3H), 2.85 (m, 3H), 3.58 (br, 2H), 3.76 (s, 3H), 3.88 (m, 2H), 4.00 (m, 1H), 6.65 (d, 2H), 6.82 (s, 4H), 6.99 (d, 2H);

Analysis for $C_{18}H_{24}N_2N_2O_3$ Calc'd: C, 68.33; H, 7.65; N, 8.85. Found: C, 68.07; H, 7.61; N, 9.13.

Step c) tert-Butyl 4-aminophenethyl[(2S)-2-hydroxy-3-(4-methoxyphenoxy)propyl]carbamate This compound was prepared from (2S)-1-[(4-aminophenethyl)amino]-3-(4-methoxyphenoxy)-2-propanol and di-tert-butyl dicarbonate in substantially the same manner as described in example 1, step c, and was obtained as a colorless oil (57% yield): MS m/e 416 (M+H)$^+$,; $^1$H NMR (CDCl$_3$ 300 MHz) δ1.45 (s, 9H), 2.71 (m, 2H), 3.44 (m, 4H), 3.57 (br, 2H), 3.76 (s, 3H), 3.81 (m, 1H), 3.82 (m, 1H), 4.08 (m, 2H), 6.62 (d, 2H), 6.91 (s, 4H), 6.93 (d, 2H);

Analysis for $C_{23}H_{32}N_2O_5$ Calc'd: C, 66.32; H, 7.74; N, 6.72. Found: C, 66.18; H, 7.75; N,6.64.

Step d) tert-Butyl 4-[(2,4-dioxo-1,3-thiazolidin-5-yl)amino]phenethyl[(2S)-2-hydroxy-3-(4-methoxyphenoxy)propyl]carbamate This compound was prepared from tert-butyl 4-aminophenethyl[(2S)-2-hydroxy-3-(4-methoxyphenoxy)propyl]carbamate and 5-bromo-1,3-thiazolidine-2,4-dione in substantially the same manner as described in example 1, step d, and was obtained as a yellow solid (60% yield); MS m/e 532 (M+H)$^+$; $^1$H NMR (DMSO-d$_6$ 300 MHz) δ1.33 (s, 9H), 3.08 (br, 1H), 3.38 (m, 4H), 3.75 (s, 3H), 3.76 (m, 1H), 3.92 (m, 1H), 5.10 (m, 1H), 6.45 (d, 1H), 6.61 (d, 2H), 6.83 (s, 4H), 6.99 (d, 2H), 12.16 (s, 1H), other $^1$H exchangeable are broad;

Analysis for $C_{26}H_{33}N_3O_7S$ Calc'd: C, 58.74; H, 6.26; N, 7.90. Found: C, 58.10; H, 6.33; N, 8.40.

Step e) 5-[4-(2-{[(2S)-2-Hydroxy-3-(4-methoxyphenoxy)propyl]amino}ethyl)anilino]-1,3-thiazolidine-2,4-dione This compound was prepared from tert-butyl 4-[(2,4-dioxo-1,3-thiazolidin-5-yl)amino]phenethyl[(2S)-2-hydroxy-3-(4-methoxyphenoxy)propyl]carbamate and trifluoroacetic acid in substantially the same manner as described in example 1, step e, and was obtained as a light yellow solid (60% yield): mp 56° C.; MS m/e 432 (M+H)$^+$; $^1$H NMR (DMSO-d$_6$ 300 MHz) δ2.87 (m, 2H), 3.17(m, 1H), 3.19 (m, 3H), 3.70 (s, 3H), 3.90 (br 2H), 4.13 (br, 1H) 5.87 (d, 1H), 6.65 (d, 1H), 6.67 (d, 2H), 6.88 (s, 4H), 7.08 (m, 3H), 8.58 (br, 2H), 12.21 (br, 1H);

Analysis for $C_{21}H_{25}N_3O_5S \times 1CF_3COOH \times 0.78\ H_2O$ Calc'd: C, 49.37; H, 4.96; N, 7.51. Found: C, 48.35; H, 4.33; N, 7.02.

EXAMPLE 11

5-{4-[2-({(2S)-3-[3-(Benzyloxy)phenoxy]-2-hydroxypropyl}amino)ethyl]anilino}-1,3-thiazolidine-2,4-dione Step a) (2S)-2-{[3-(Benzyloxy)phenoxy]methyl}oxirane This compound was prepared from 3-benzyloxyphenol and (2S)(+)oxiranylmethyl 3-nitrobenzenesulfonate in substantially the same manner as described in example 1, step a, and was obtained as a colorless oil (47% yield): MS m/e 256 M$^+$; $^1$H NMR (DMSO-d$_6$ 300 MHz), δ2.67 (m, 1H) 2.80 (m, 1H), 3.30 (m, 1H), 3.80 (m, 3H), 4.27 (m, 1H), 5.07 (s, 2H), 6.54 (m, 1H), 6.60 (m, 2H), 7.19 (m, 1H), 7.39 (m, 5H).

Step b) (2S)-1-[(4-Aminophenethyl)amino]-3-[3-(benzyloxy)phenoxy]-2-propanol

This compound was prepared from (2S)-2-{[(3-(benzyloxy)phenoxy]methyl}oxirane and 4-(2-aminoethyl) aniline as described in example 1, step b, with one modification, the mixture was stirred at 70° C. in tetrahydrofuran. The solvent was removed under vacuo and the product was triturated with ethyl ether to give a white solid (67% yield): MS m/e 392 M$^+$; $^1$H NMR (CDCl$_3$ 300 MHz) δ1;6 (br, 1H), 2.69 (m, 3H), 2.85 (m, 3H), 3.30 (br, 1H), 3.55 (s, 2H), 3.92 (m, 2H), 4.00 (m, 1H), 5.03 (s, 2H), 6.59 (m, 5H), 7.00 (d, 2H), 7.19 (t, 1H), 7.40 (m, 5H);

Analysis for $C_{24}H_{28}N_2O_3$ Calc'd: C, 73.44; H, 7.19; N, 7.14. Found: C, 73.12; H, 7.06; N, 7.15.

Step c) tert-Butyl 4-aminophenethyl{(2S)-3-[3-(benzyloxy)phenoxy]-2-hydroxypropyl}carbamate This compound was prepared from (2S)-1-[(4-aminophenethyl)amino]-3-[3-(benzyloxy)phenoxy]-2-propanol and di-tert-butyl dicarbonate in substantially the same manner as described in example 1, step c, and was obtained as a light yellow oil (57% yield): MS m/e 493 (M+H)$^+$; $^1$H NMR (CDCl$_3$ 300 MHz) δ1.58 (s, 9H), 2.71 (m, 2H), 3.41 (m, 4H), 3.55 (br, 2H), 3.84 (br, 1H), 3.92 (br, 1H), 4.09 (m, 2H), 5.04 (s, 2H), 6.59 (m, 5H), 6.93 (d, 2H), 7.19 (t, 1H), 7.38 (m, 5H);

Analysis for C29H36N$_2$O$_5$ Calc'd: C, 70.71; H, 7.37; N, 5.69. Found: C, 69.95; H, 7.20; N, 5.40.

Step d) tert-Butyl (2S)-3-[3-(benzyloxy)phenoxy]-2-hydroxypropyl{4-[(2,4-dioxo-1,3-thiazolidin-5-yl)amino]phenethyl}carbamate This compound was prepared from tert-butyl 4-aminophenethyl{(2S)-3-[3-(benzyloxy)phenoxy]-2-hydroxypropyl}carbamate and 5-bromo-1,3-thiazolidine-2,4-dione in substantially the same manner as described in example1, step d, and was obtained as a yellow solid (83%yield): MS m/e 608 (M+H)$^+$; $^1$H NMR (DMSO-d$_6$ 300 MHz) δ1.33 (s, 9H), 2.64 (m, 2H), 3.27 (br, 1H), 3.34(m, 3H), 3.82 (m, 2H), 3.93 (m, 1H), 5.06 (s, 2H), 5.12 (m, 1H), 6.49 (m, 6H), 6.99 (m, 2H), 7.17 (t, 1H), 7.38 (m, 6H), 12.16 (s, 1H);

Analysis for $C_{32}H_{37}N_3O_7S$ Calc'd: C, 63.24; H, 6.14; N, 6.91. Found: C, 62.50; H, 6.33; N, 7.15.

Step e ) 5-{4-[2-({(2S)-3-[3-(Benzyloxy)phenoxy]-2-hydroxypropyl}amino)ethyl]anilino}-1,3-thiazolidine-2,4-dione This compound was prepared from tert-butyl (2S)-3-[3-(benzyloxy)phenoxy]-2-hydroxypropyl{4-[(2,4-dioxo-1,3-thiazolidin-5-yl)amino]phenethyl}carbamate and trifluoroacetic acid in substantially the same manner as described in example 1, step e, and was obtained as a light yellow solid (23%yield): mp 53° C.; MS m/e 508 (M+H)$^+$,; $^1$H NMR (DMSO-d$_6$ 300 MHz) δ2.86 (m, 2H), 3.06 (m, 2H), 3.20 (m, 3H), 3.96 (s, 2H), 4.15 (br 1H), 5.09 (s, 2H) 5.98 (br, 1H), 6.59 (m, 5H), 7.07 (m, 2H), 7.20 (t, 1H), 7.43 (m, 5H), 8.58 (br, 2H), 12.21 (br, 1 H);

Analysis for $C_{27}H29N_3O_5S \times 1CF_3COOH \times 0.97\ H_2O$ Calc'd: C, 54.50; H, 45.04; N, 6.76. Found: C, 54.13; H, 5.02; N, 6.10.

EXAMPLE 12

5-[4-(2-{[(2S)-2-Hydroxy-3-(3-hydroxyphenoxy)propyl]amino}ethyl)anilino]-1,3-thiazolidine-2,4-dione Step a) tert-butyl 4-aminophenethyl[(2S)-2-hydroxy-3-(3-hydroxyphenoxy)propyl]carbamate This compound was prepared from tert-butyl 4-aminophenethyl{(2S)-3-[3-(benzyloxy)phenoxy]-2-hydroxypropyl}carbamate in substantially the same manner as described in example 5, step a, and was obtained as a white solid (73% yield): MS m/s 403 (M+H)$^+$; $^1$H NMR (DMSO-d$_6$ 300 MHz) δ1.36 (s, 9H),2 .58 (t, 2H), 3.07(m, 1H), 3.28 (m, 3H), 3.74 (m, 2H), 4.83 (s, 2H), 5.07 (br, 1H), 4.95 (br, 1H), 6.32 (m, 3H), 6.45 (d, 2H), 6.80 (d, 2H), 7.02 (t, 1H), 9.34 (s, 1 H).

Step b) tert-Butyl 4-[(2,4-dioxo-1,3-thiazolidin-5-yl)amino]phenethyl[(2S)-2-hydroxy-3-(3-hydroxyphenoxy)propyl]carbamate This compound was prepared from tert-butyl 4-aminophenethyl[(2S)-2-hydroxy-3-(3-hydroxyphenoxy)propyl]carbamate and 5-bromo-1,3-thiazolidine-2,4-dione in substantially the same manner as described in example 1, step d, and was obtained as a yellow solid (89% yield): MS m/e 518 (M+H)$^+$; H NMR (DMSO-d$_6$ 300 MHz) δ1.35 (s, 9H), 3.01 (br, 1H), 3.31 m, 2H), 3.76 (m, 2H), 3.94 (m, 1H), 5.11 (br, 1H), 6.32 (m, 3H), 6.50 (d, 1H), 6.62 (d, 2H), 7.03 (m, 4H), 9.36 (s, 1H), 12.18 (s, 1H).

Step c) 5-[4-(2-{[(2S)-2-Hydroxy-3-(3-hydroxyphenoxy)propyl]amino}ethyl)anilino]-1,3-thiazolidine-2,4-dione This compound was prepared from tert-butyl 4-[(2,4-dioxo-1,3-thiazolidin-5-yl)amino]phenethyl[(2S)-2-hydroxy-3-(3-hydroxyphenoxy)propyl]carbamate and trifluoroacetic acid as described in example 1, step e, with one change, he product was purified by reverse HPLC to give an off white solid (22% yield): mp 65° C.; MS m/418 (M+H)$^+$; $^1$H NMR (DMSO-d$_6$ 300 MHz) δ2.82 (m, 2H), 3.05 (m, 1H), 3.20 (m, 3H), 3.89 (m, 2H), 4.14 (br 1H), 5.87 (s, 1H), 6.36 (m, 3H), 6.49 (d, 1H), 6.66 (d, 2H), 7.08 (m, 4H), 8.59 (s, 2H), 9.48 (s, 1H), 12.21 (s, 1 H);

Analysis for $C_{20}H_{23}N_3O_5S \times 1CF_3COOH \times 2.47\ H_2O$ Calc'd: C, 45.83, H, 5.03, 7.29. Found: C, 45.03, H, 4.37, N, 7.24.

EXAMPLE 13

5-[4-(2-{[(2S)-3-(9*Carbazol-4-yloxy)-2-hydroxypropyl]amino}ethyl)anilino]-1,3thiazolidine-2,4-dione Step a) (2S)-1-[(4-Aminophenethyl)amino]-3-(9Scarbazol-4-yloxy)-2-propanol This compound was prepared from 9H-carbazol-4-yl (2S) oxiranylmethyl ether and 4-(2-aminoethyl)aniline as described in example 1, step b, with one change, the product was purified by flash chromatography (dichloromethane/methanol 9.5/0.5) and recrystallized from tetrahydrofuran/toluene to give an off white solid (67% yield): MS m/e 376 (M+H)$^+$,: $^1$H NMR (CDCl$_3$ 300 MHz) δ1.80 (br, 1H), 2.71 (m, 2H), 2.90 (m, 3H), 3.06 (m, 1H), 3.55 (br, 2H), 4.22 (m, 3H), 6.60 (d, 2H), 6.61 (d, 1H), -p0 - - - p7.01 (d, 2H), 7.25 (d, 1H), 7.26 (m, 5H), 8.09 (s, 1H), 8.26(s, 1H);

Analysis for $C_{23}H_{25}N_3O_2$ Calc'd: C, 73.57; H, 6.71; N, 11.19. Found: C, 73.41; H, 6.82; N, 11.00.

Step b) tert-Butyl 4-aminophenethyl[(2S)-3-(9H-carbazol-4-yloxy)-2-hydroxypropyl]carbamate This compound was prepared from (2S)-1-[(4-aminophenethyl)amino]-3-(9H-carbazol-4-yloxy)-2-propanol and di-tert-butyl dicarbonate in substantially the same manner as described in example 1, step c, and was obtained as a white shiny solid (56% yield): MS m/e 476 (M+H)$^+$; $^1$H NMR (DMSO d$_6$ 300 MHz) δ1.35 (s, 9H), 2.50 (m, 2H), 3.28 (m, 3H), 3.49 (dd, 1H), 4.08 (m, 2H), 4.14 (m, 1H), 4.81 (s, 2H), 5.25 (d, 1H), 6.41 (d, 2H), 6.64 (d, 1H), 6.69 (m, 2H), 7.04 (d, 1H), 7.06 (t, 1H), 7.24, (t, 1H), 7.26 (t, 1H), 7.28 (d, 1H), 8.30 (dd, 1H), 11.22 (s, 1H);

Analysis for $C_{28}H_{33}N_3O_4$ Calc'd: C, 70.71; H, 6.99; N, 8.84. Found: C, 69.94; H, 7.39; N, 8.57.

Step c) tert-Butyl (2S)-3-(9H-carbazol-4-yloxy)-2-hydroxypropyl{4-[(2,4-dioxo-1,3-thiazolidin-5-yl)amino]phenethyl}carbamate This compound was prepared from tert-butyl 4-aminophenethyl[(2S)-3-(9H-carbazol-4-yloxy)-2-hydroxypropyl]carbamate and 5-bromo-1,3-thiazolidine-2,4-dione in substantially the same manner as described in example 1, step d, and was obtained as a yellow solid (50% yield): MS m/e 591 (M+H)$^+$; $^1$H NMR (DMSO-d$_6$ 300 MHz) δ1.35 (s, 9H), 2.66 (t, 2H), 3.28 (m, 2H), 3.31 m, 2H), 3.39 (m, 2H), 4.10 (m, 2H), 4.20 (m, 1H), 5.29, (d, 2H), 6.45 (d, 1H), 6.57 (d, 2H), 6.64 (d, 1H), 6.98 (m, 2H), 7.06 (d, 1H), 7.08 (t, 1H), 7.26 (t, 1H), 7.28 (t, 1H), 7.44 (d, 1H), 8.31 (m, 1H), 11.24 (s, 1H), 12.17 (s 1H).

Step d) 5-[4-(2-{[(2S)-3-(9H-Carbazol-4-yloxy)-2-hydroxypropyl]amino}ethyl)anilino]-1,3-thiazolidine-2,4-dione This compound was prepared from tert-butyl (2S)-3-(9H-carbazol-4-yloxy)-2-hydroxypropyl{4-[(2,4-dioxo-1,3-thiazolidin-5-yl)amino]phenethyl}carbamate and trifluoroacetic acid in substantially the same manner as described in example 1, step e, to give an off white solid (22% yield): mp 140° C.; MS m/e 491 (M+H)$^+$; $^1$H NMR (DMSO-d$_6$ 300 MHz) δ2.48 (m, 2H), 3.21 (m, 3H), 3.40 (m, 2H), 4.20 (m, 2H), 4.38 (br, 1H), 6.01 (br, 1H), 6.47 (d, 1H), 6.63 (m, 3H), 7.08 (m, 4H), 7.35 (m, 2H), 7.43 (d, 1H), 8.21 (d, 1H), 8.66 (br, 2H), 11.28 (s, 1H), 12.21 (s, 1H);

Analysis for $C_{26}H_{26}N_4O_4S \times 1\ CF_3COOH \times 1\ H_2O$ Calc'd: C, 55.63; H, 4.80; N, 10,23. Found: C, 55.77; H, 4.81; N, 8.92.

EXAMPLE 14

N-{5-[(1S)-2-({4-[(2,4-Dioxo-1,3-thiazolidin-5-yl)amino]phenethyl}amino)-1-hydroxyethyl]-2-hydroxyphenyl}methanesulfonamide Step a) N-[2-(Benzyloxy)-5-((1S)-2-bromo-1-{[tert-butyl(dimethyl)silyl]oxy}ethyl)phenyl]methanesulfonamide A solution of tert-butyldimethylsilyl triflate (11.25 mL, 5.41 mmol) in dichloromethane (10 mL) was added slowly into a cold (−78° C.) mixture of N-{2-(benzyloxy)-5-[(1S)-2-bromo-1-hydroxyethyl]phenyl}methanesulfonamide (1.93 g, 4.82 mmol), 2,6 lutidine (1.08 mL, 9.64 mmol) and dichloromethane(30 mL). The new mixture was warmed up to room temperature, stirred for 4 hours, poured into a saturated aqueous bicarbonate solution, and extracted with ethyl ether. The organic extracts were washed with brine, and dried over MgSO$_4$. Evaporation and purification by flash chromatography (hexanes/ethyl acetate 9/1) gave a white solid (1.55 g, 62% yield): MS m/e 513M$^+$; $^1$H NMR (DMSO-d$_6$ 300 MHz) δ0.10 (s, 3H), 0.16 (s, 3H), 0.84(s, 9H), 2.88 (s, 3H), 3.56 (m, 2H), 4.88 (m, 1H), 5.14 (s, 2H), 7.11 (d, 1H), 7.16 (d, 1H), 7.32 (m, 2H), 7.38 (m, 2H), 7.51 (d, 2H), 8.90 (s, 1H);

Analysis for $C_{24}H_{29}N_3O_4S$ Calc'd: C, 51.35; H, 6.27; N, 2.72. Found: C, 50.02; H, 6.27; N, 2.53.

Step b) N-[5-((1S)-2-[(4-Aminophenethyl)amino]-1-{[tert-butyl(dimethyl)silyl]oxy}ethyl)-2-(benzyloxy)phenyl]methanesulfonamide A mixture of N-[2-(benzyloxy)-5-((1S)-2-bromo-1-{[tert-butyl(dimethyl)silyl]oxy}ethyl)phenyl]methanesulfonamide (1.55 g, 3.012 mmol), 4-(2-aminoethyl)aniline (0.53 g, 3.915 mmol), diisopropyl amine (2.4 ml, 19.60 mmol), sodium iodide (0.04 g) and tetrahydrofuran (5 mL) was stirred in a sealed flask at 100° C. for 48 hours. The mixture was cooled to room temperature, diluted with ethyl acetate, washed with aqueous brine solution, and dried over MgSO$_4$. Evaporation and purification by flash chromatography (hexanes/ethyl acetate/methanol/triethylamine 7/2/0.95/0.05) gave a white solid (1.25 g, 72%): MS m/e 371 (M+H)$^+$; $^1$H NMR (DMSO-d$_6$ 300 MHz) δ0.10 (s, 3H), 0.16 (s, 3H), 0.84 (s, 9H), 2.65 (m, 6H), 2.83 (s, 3H), 4.65 (m, 1H), 4.80 (s, 2H), 5.18 (s, 2H), 6.42 (d, 2H), 6.80 (d, 2H), 7.15 (s, 2H), 7.21 (s, 1H), 7.35 (m, 4H), 7.50 (d, 2H), 8.8 (br, 1H);

Analysis for $C_{29}H_{43}N_3O_4$ SSi Calc'd: C, 63.18; H, 7.54; N, 7.37. Found: C, 62.41; H, 7.45; N, 7.11.

Step c) N-[5-{(1S)-2-[(4-Aminophenethyl)amino]-1-[(triethylsilyl)oxy]ethyl}-2-(benzyloxy)phenyl]methanesulfonamide This compound was prepared from N-(2-(benzyloxy)-5-{2-iodo-1-[(triethylsilyl)oxy]ethyl}phenyl) methanesulfonamide and 4-(2-aminoethyl)aniline, as described in example 1, step b, without the present of sodium iodide to give a white solid (79% yield): MS m/e 570 (M+H)$^+$; $^1$H NMR (DMSO-d$_6$ 300 MHz) δ0.77 (m, 6H), 0.79 (m, 9H), 2.64 (m, 6H), 2.84 (s, 3H), 4.65 (m, 1H), 4.80 (d, 2H),5.13 (s, 2H), 6.44 (d, 2H), 6.79 (d, 2H) 7.06 (m, 3H), 7.24 (s, 1H), 7.25 (m, 1H), 7.38 (m, 2H), 7.51 (d, 2H), 8.40 (br, 1 H);

Analysis for C$_{30}$H$_{43}$N$_3$O SSi Calc'd: C, 63.18; H, 7.54; N, 7.37. Found: C, 62.20; H, 7.39; N, 7.30.

Step d) N-[5-{(1S)-2-[(4-Aminophenethyl)amino]-1-hydroxyethyl}-2-(benzyloxy)phenyl]methanesulfonamide A mixture of N-[5-{(1S)-2-[(4-aminophenethyl)amino]-1-[(triethylsilyl)oxy]ethyl}-2-(benzyloxy)phenyl]methanesulfonamide (2.2 g, 4.28 mmol), tetrabutylammonium fluoride: 1.0 M solution in tetrahydrofuran (20 ml) and terahydrofuran (15 ml) was stirred at ambient temperature for 48 hours, poured into water, basified with saturated bicarbonate solution, and extracted with ethyl acetate. The organic extracts were washed with aqueous brine solution, and dried over MgSO$_4$. Evaporation and recrystallization from ethyl acetate gave a white solid (1.5 g, 78% yield): MS m/e 456 (M+H)$^+$; $^1$H NMR (DMSO-d$_6$ 300 MHz) δ2.65 (m, 6H), 2.83 (s, 3H), 3.18 (m, 1H), 4.65 (m, 1H), 4.80 (s, 2H), 5.18 (s, 2H), 5.20 (m, 1H), 6.42 (d, 2H), 6.80 (d, 2H), 7.15 (m, 2H), 7.21 (s, 1H), 7.35 (m, 1H), 7.41 (t, 2H),7.56 (d, 2H), 8.30 (br, 1H);

Analysis for C$_{24}$H$_{29}$N$_3$O$_4$ S Calc'd: C, 63.22; H, 6.36; N, 9.22. Found: C, 62.57; H, 6.55; N, 8.81.

Step e) N-(5-{(1S)-2-[(4-Aminophenethyl)amino]-1-hydroxyethyl}-2-hydroxyphenyl)methanesulfonamide This compound was prepared from N-[5-{(1S)-2-[(4-aminophenethyl)amino]-1-hydroxyethyl}-2-(benzyloxy)phenyl]methanesulfonamide in substantially the same manner, as described in example 2, step a, with one change; the compound was recrystallized from ethanol and ethyl acetate to give a white solid (80% yield): MS m/s 366 (M+H)$^+$; $^1$H NMR (DMSO d$_6$ 300 MHz) δ2.48 (m, 2H), 2.59 (d, 2H), 2.67 (m, 2H), 2.89 (s, 3H), 4.45 (t, 1H), 4.79 (s, 2H), 6.44 (d, 2H), 6.82 (m, 3H), 6.93 (d, 2H), 7.13 (s, 1H), all $^1$H exchangeable are broad.

Step f) tert-Butyl 4-[(2,4-dioxo-1,3-thiazolidin-5-yl)amino]phenethyl((2S)-2-hydroxy-2-{4-hydroxy-3-[(methylsulfonyl)amino]phenyl}ethyl)carbamate This compound was prepared from N-(5-{(1S)-2-[(4-aminophenethyl)amino]-1-hydroxyethyl}-2-hydroxyphenyl)methanesulfonamide and di-tert-butyl dicarbonate in substantially the same manner as described in example 1, step c, and was obtained as an off white solid (64% yield): MS m/e 466 (M+H)$^+$; $^1$H NMR (DMSO d$_6$ 300 MHz) δ1.35 (s, 9H), 2.88 (s, 3H), 3.01 (m, 2H), 3.03 (m, 2H), 4.57 (m, 1H), 4.81(s, 2H), 5.30 (dd, 1H), 6.45 (d, 2H), 6.80 (m, 1H), 6.82 (d, 2H), 6.94 (t, 1H), 7.13 (s, 1H), 8.59 (s, 1H), 9.69 (s, 1H).

Step g) tert-Butyl 4-[(2,4-dioxo-1,3-thiazolidin-5-yl)amino]phenethyl((2S)-2-hydroxy-2-{4-hydroxy-3-[(methylsulfonyl)amino]phenyl}ethyl)carbamate This compound was prepared from tert-butyl 4-[(2,4-dioxo-1,3-thiazolidin-5-yl)amino]phenethyl((2S)-2-hydroxy-2-{4-hydroxy-3-[(methylsulfonyl)amino]phenyl}ethyl)carbamate and 5-bromo-1,3-thiazolidine-2,4-dione in substantially the same manner as described in example 1, step d, and was obtained as a yellow solid (46% yield): MS m/e 581 (M+H)$^+$; $^1$H NMR (DMSO-d$_6$ 300 MHz) δ1.35 (d, 9H), 2.49 (m, 2H), 2.88 (s, 3H), 3.27 (m, 4H), 4.59 (m, 1H), 5.28 (dd, 1H), 6.47 (d, 1H), 6.59, (d, 2H), 6.84 (m, 1H), 6.96 (m, 3H), 7.14 (t, 1H), 7.23 (m, 1H), 8.61 (s, 1H), 9.71 (s, 1H), 12.23 (s, 1 H).

Step h) N-{5-[(1S)-2-({4-[(2,4-Dioxo-1,3-thiazolidin-5-yl)amino]phenethyl}amino)-1-hydroxyethyl]-2-hydroxyphenyl}methanesulfonamide This compound was prepared from tert-butyl 4-[(2,4-dioxo-1,3-thiazolidin-5-yl)amino]phenethyl((2S)-2-hydroxy-2-{4-hydroxy-3-[(methylsulfonyl)amino]phenyl}ethyl)carbamate and trifluoroacetic acid in substantially the same manner as described in example 1, step e, to give an off white solid (22% yield): mp 130° C.; MS m/e 481 (M+H)$^+$; $^1$H NMR (DMSO-d$_6$ 300 MHz) δ2.83 (m, 2H), 2.95 (m, 3H), 3.09 (m, 1H), 3.10 (br, 3H), 4.78 (d, 1H), 6.7 (s, 1H), 6.47 (d, 1H), 6.65 (d, 2H), 6.89 (d, 1H), 7.05 (m, 4H), 7.23 (s, 1H), 8.57 (br, 2H), 8.74 (s, 1H), 9.96 (s, 1H), 12.20 (s, 1H);

Analysis for C$_{20}$H$_{24}$N$_4$O$_6$S$_2$×1 CF$_3$COOH×1.87 H$_2$O Calc'd: C, 55.63; H, 4.80; N, 10,23. Found: C, 55.77; H, 4.81, N, 8.92.

EXAMPLE 15

5-[4-(2-{[(2S)-3-(1-Benzofuran-5-yloxy)-2-hydroxypropyl]amino}ethyl)anilino]-1,3-thiazolidine-2,4-dione Step a) 4-Hydroxybenzofuran A solution of boron tribromide: 1.0 M solution in methylene chloride (95 ml) was added slowly into a cold (−78° C.) solution of 5-methoxybezofuran (10 g, 67.5 mmol) in dichloromethane(100 mL). The new mixture was warmed up to room temperature, stirred for 18 hours, poured into a saturated aqueous bicarbonate solution, and extracted with ethyl acetate. The organic extracts were washed with brine, dried over MgSO$_4$. Evaporation and purification by flash chromatography (hexanes/ethyl acetate 9/1) gave a white solid (5.9 g, 65%): MS m/e 133 (M−H)$^+$; $^1$H NMR (DMSO-d$_6$ 300 MHz) δ6.72 (m, 1H), 6.78 (d, 1H), 6.94 (d, 1H), 7.35 (d, 1), 781, (s, 1H), 8.18 (s, 1H).

Step b) 1-Benzofuran-5-yl (2R)-oxiranylmethyl ether

This compound was prepared from 4-hydroxybenzofuran and (2S)-(+)oxiranylmethyl 3-nitrobenzenesulfonate in substantially the same manner as described in example 1, step a, and was obtained as colorless oil (38% yield): MS m/e 190 (M )$^+$,; $^1$H NMR (DMSO-d$_6$ 300 MHz): δ2.71 (m, 1H) 2.85 (m, 1H), 3.34 (m, 1H), 3.85 (m, 1H), 4.33 (m, 1H), 6.88 (s, 1H), 6.94 (d, 1H), 7.16 (s, 1H), 7.48 (d, 1H), 7.94 (s, 1H).

Step c) (2S)-1-[(4-Aminophenethyl)amino]-3-(1-benzofuran-5-yloxy)-2-propanol

This compound was prepared from 1-benzofuran-5-yl (2R)oxiranylmethyl ether and 4-(2-aminoethyl)aniline as described in example 1, step b, with one modification, the mixture was stirred at 70° C. in tetrahydrofuran for 48 hours. The solvent was removed in vacuo and the product was triturated with ethyl ether to give a white solid (25% yield): MS m/e 326 M$^+$; $^1$H NMR (CDCl$_3$ 300 MHz) δ2.61 (br, 1H), 2.83 (m, 6H), 3.57 (s, 3H), 4.01 (m, 3H), 6.63 (m, 2H), 6.65 (s, 1H), 6.88 (m, 1H), 6.98 (m, 2H), 7.00 (m, 1H), 7.25 (d, 1H), 7.39 (s, 1H);

Analysis for C$_{19}$H$_{22}$N$_2$O$_3$ Calc'd: C, 69.92; H, 6.79; N, 8.58. Found: C, 69.74; H, 6.77; N, 9.10.

Step d) tert-Butyl 4-aminophenethyl[(2S)-3-(1-benzofuran-5-yloxy)-2-hydroxypropyl]carbamate This compound was prepared (2S)-1-[(4-aminophenethyl)amino]-3-(1-benzofuran-5-yloxy)-2-propanol and di-tert-butyl dicarbonate in substantially the same manner as described in example 1, step c, and was obtained as a light yellow oil (48% yield): MS m/e 426 (M)+; $^1$H NMR (CDCl$_3$ 300 MHz) δ1.44 (s, 9H), 2.72 (m, 2H), 3.44 (m, 4H), 3.60 (br, 2H), 3.90 (br, 1H),3.98 (br, 1H), 4.09 (m, 2H), 6.60 (m, 2H), 6.70 (s, 1H), 6.92 (m 3H), 7.05 (s, 1H), 7.40 (d, 1H), 7.60 (s, 1h).

Step e) tert-Butyl (2S)-3-(1-benzofuran-5-yloxy)-2-hydroxypropyl{4-[(2,4-dioxo-1,3-thiazolidin-5-yl)amino]phenethyl}carbamate This compound was prepared from tert-butyl 4-aminophenethyl[(2S)-3-(1-benzofuran-5-yloxy)-2-hydroxypropyl]carbamate and 5-bromo-1,3-thiazolidine-2,4-dione in substantially the same manner as described in example 1, step d, and was obtained as yellow solid (50% yield), MS m/e 591 (M+H)+, $^1$H NMR (DMSO-d$_6$ 300 MHz) δ1.35 (s, 9H), 2.66 (m, 3H), 3.40 (m, 3H), 3.98 (m, 3H), 5.14 (br, 1H), 6.59 (d, 2H), 6.61 (d, 1H), 6.85 (m, 2H), 6.99 (m, 3H), 7.13 (s, 1H), 7.45 (d, 1H),7.91 (s, 1H), 12.16 (br, 1H).

Step f) 5-[4-(2-{[(2S)-3-(1-Benzofuran-5-yloxy)-2-hydroxypropyl]amino}ethyl)anilino]-1,3-thiazolidine-2,4-dione This compound was prepared from tert-butyl (2S)-3-(1-benzofuran-5-yloxy)-2-hydroxypropyl{4-[(2,4-dioxo-1,3-thiazolidin-5-yl)amino]phenethyl}carbamate and trifluoroacetic acid as described in example 1, step e, with one change, the product was purified by reverse HPLC to give an off white solid (10% yield): mp 50° C.; MS m/e 442 (M+H)+; $^1$H NMR (DMSO-d$_6$ 300 MHz) δ2.86 (m, 2H), 3.23 (m, 4H), 3.99 (m, 2H), 4.16 (m, 1H), 5.85 (br, 1H), 6.48 (d, 1H), 6.65 (d, 2H), 6.87 (m, 2H), 7.07 (m, 3H), 7.18 (s, 1H), 7.48 (d, 1H), 7.94 (s, 1H), 8.60 (br, 2H), 12.20 (s, 1H);

Analysis for C$_{22}$H$_{23}$N$_3$O$_5$S×1.3 CF$_3$COOH×1.25 H$_2$O Calc'd: C, 48.21; H, 4.16; N, 6.86. Found: C, 46.44; H, 4.16; N, 6.86.

EXAMPLE 16

5-[4-(2-{[(2S)-3-(4-Butoxyphenoxy)-2-hydroxypropyl]amino}ethyl)anilino]-1,3-thiazolidine-2,4-dione Step a) (2R)-2-[(4-Butoxyphenoxy)methyl]oxirane This compound was prepared from 4-butoxyphenol and (2S)-(+)oxiranylmethyl 3-nitrobenzenesulfonate in substantially the same manner as described in example 1, step a, and was obtained as a colorless oil (51% yield): MS m/e 222 M+; $^1$H NMR (DMSO-d$_6$ 300 MHz): δ0.90 (t, 3H), 1.41 (m, 2H), 1.64 (m, 2H), 2.65 (m, 1H), 2.80 (m, 1H), 3.29 (m, 1H), 3.75 (m, 1H), 3.85 (t, 2H), 4.24 (dd, 1H), 6.87 (dd, 4H);

Analysis for C$_{13}$H$_{18}$O$_3$ Calc'd: C, 70.25; H, 8.16. Found: C, 69.94 H, 8.13.

Step b) (2S)-1-[(4-Aminophenethyl)amino]-3-(4-butoxyphenoxy)-2-propanol

This compound was prepared from (2R)-2-[(4-butoxyphenoxy)methyl]oxirane and 4-(2-aminoethyl)aniline as described in example 1, step b, with one modification, the mixture was stirred at 70° C. in tetrahydrofuran for 48 hours. The solvent was removed in vacuo and the product was triturated with ethyl ether to give a white solid (49% yield): MS m/e 286 (M)+; $^1$H NMR (CDCl$_3$ 300 MHz) δ0.96 (t, 3H) 1.46 (m, 2H), 1.75 (m, 2H), 1.85 (br, 1H), 2.69 (m, 3H), 2.82 (m, 3H), 3.57 (br, 2H), 3.88 (m, 5H), 3.98 (m, 1H), 6.61 (d, 2H), 6.81 (s, 4H), 6.99 (d, 2H);

Analysis for C$_{21}$H$_{30}$N$_2$O$_3$ Calc'd: C, 70.29; H, 7.79; N, 7.81. Found: C, 70.20; H, 8.32 N, 7.86.

Step c) tert-Butyl 4-aminophenethyl[(2S)-3-(4-butoxyphenoxy)-2-hydroxypropyl]carbamate This compound was prepared from (2S)-1-[(4-aminophenethyl)amino]-3-(4-butoxyphenoxy)-2-propanol and di-tert-butyl dicarbonate in substantially the same manner as described in example 1, step c, and was obtained as a colorless oil (66% yield), MS m/e 459 (M+H)+; $^1$H NMR (CDCl$_3$ 300 MHz) δ0.96 (t, 3H), 1.45 (s, 9H), 1.46 (m, 2H), 1.74 (m, 2H), 2.70 (m, 2H), 3.39 (m, 4H), 3.57 (br, 2H), 3.88 (m, 1H), 3.90 (m, 3H), 4.09 (br, 2H), 6.60 (d, 2H), 6.81 (s, 4H), 6.93 (d, 2H);

Analysis for C$_{26}$H$_{38}$N$_2$O$_5$×0.6 C$_4$H$_8$O$_2$ Calc'd: C, 66.66; H, 7.68; N, 5.66. Found: C, 65.32; H, 7.95; N, 5.69.

Step d) tert-Butyl (2S)-3-(4-butoxyphenoxy)-2-hydroxypropyl{4-[(2,4-dioxo-1,3-thiazolidin-5-yl)amino]phenethyl}carbamate This compound was prepared from tert-butyl 4-aminophenethyl[(2S)-3-(4-butoxyphenoxy)-2-hydroxypropyl]carbamate and 5-bromo-1,3-thiazolidine-2,4-dione in substantially the same manner as described in example 1, step d, and was obtained as a light yellow solid (63% yield): MS m/e 573 (M)+; $^1$H NMR (DMSO-d$_6$ 300 MHz) δ0.93 (t, 3H), 1.35(s, 9H), 1.42 (m, 2H), 1.67 (m, 2H), 2.65 (m, 1H), 3.05 (br, 1H), 3.29 (m, 2H), 3.35 (m, 2H), 3.76 (m, 2H), 3.88 (m, 2H), 5.10 (br, 1H), 6.47 (d, 1H), 6.83 (d, 2H), 6.99 (s, 4H), 7.01 (m, 3H), 12.16 (s, 1H);

Analysis for C$_{29}$H$_{39}$N$_3$O$_3$S Calc'd: C, 60.71; H, 6.85; N, 7. Found: C, 60.44; H, 6.83; N, 7.32.

Step e) 5-[4-(2-{[(2S)-3-(4-Butoxyphenoxy)-2-hydroxypropyl]amino}ethyl)anilino]-1,3-thiazolidine-2,4-dione This compound was prepared from tert-butyl (2S)-3-(4-butoxyphenoxy)-2-hydroxypropyl{4-[(2,4-dioxo-1,3-thiazolidin-5-yl)amino]phenethyl}carbamate and trifluoroacetic acid in substantially the same manner as described in example 1, step e, and was obtained as a light yellow solid (72% yield): mp 65° C.; MS m/e 447 (M+H)+; $^1$H NMR (DMSO-d$_6$ 300 MHz) δ0.93 (t, 3H), 1.41 (m, 2H), 1.64 (m, 2H), 2.85 (m, 3H), 3.01 (br, 1H), 3.89 (m, 1H), 4.09 (br, 1H), 5.84 (br, 1H), 6.50 (d, 1H), 6.65 (d, 2H), 6.85 (s, 4H), 7.06 (m, 3H), 8.56 (br, 2H), 12.21 (br, 1H);

Analysis for C$_{26}$H$_{31}$N$_3$O$_5$S×1 CF$_3$COOH Calc'd: C, 43.14,; H, 5.49; N, 7.15. Found: C, 52.60; H 5.70; N, 6.63.

EXAMPLE 17

5-[4-(2-{[(2S)-2-Hydroxy-3-phenoxypropyl]amino}ethyl)(methyl)anilino]-1,3-thiazolidine-2,4-dione Step a) (2S)-1-[(4-Nitrophenethyl)amino]-3-phenoxy-2-propanol This compound was prepared from (S)-2-(phenoxymethyl)oxirane (Example 6, step a ) and 4-nitrophenylethylamine as described in example 1, step b, with one modification, the mixture was stirred at 70° C., and was obtained as an off white solid (73% yield): MS m/e 316 M+; $^1$H NMR (CDCl$_3$ 300 MHz), 1.85 (br, 1H), 3.0 (m, 6H), 3.98 (d, 2H), 4.03 (m, 1H), 6.85 (d, 2H), 6.99 (t, 1H), 7.25 (m, 3H), 7.40 (d, 2H), 8.18 (d, 2H).

Step b) (1S)-2-[(tert-Butoxycarbonyl)(4-nitrophenethyl)amino]-1-(phenoxymethyl)ethyl tert-butyl carbonate This compound was prepared from (2S)-1-[(4-nitrophenethyl)amino]-3-phenoxy-2-propanol and di-tert-butyl dicarbonate as described in example 1, step c, with one modification, the reaction was conducted in acetonitrile in the presence of 4-(dimethylamino)pyridine, and the product was obtained as a colorless oil (68% yield): MS m/e 516 (M+H)+; $^1$H NMR (CDCl$_3$ 300 MHz) δ1.44 (s, 9H), 1.50 (s, 9H), 3.0 (br, 2H), 3.30 (br, 1H), 3.59 (br, 3H), 4.01 (m, 2H), (m, 2H), 5.08 (m, 1H), 6.85 (d, 2H), 6.97 (t, 1H), 7.25 (m, 4H), 8.18 (d, 2H);

Analysis for C$_{27}$H$_{36}$N$_2$O$_8$ Calc'd: C, 62.78; H, 7.02; N, 5.42. Found: C, 61.91; H, 7.03; N, 5.32.

Step c) (1S)-2-[(4-Aminophenethyl)(tert-butoxycarbonyl) amino]-1-(phenoxymethyl)ethyl tert-butyl carbonate A mixture of compound from 1S)-2-[(tert-butoxycarbonyl)(4-nitrophenethyl)amino]-1-(phenoxymethyl)ethyl tert-butyl carbonate (3.3 g, 6.38 mmol), 10% Pd/C (0.1 g), and ethanol (35 mL) was hydrogenated on a Parr Shaker at 40 psi for 4 hours. The catalyst was removed by filtration through celite. Evaporation of the filtrate gave a colorless oil (93% yield): MS m/s 486 (M+H)$^+$; $^1$H NMR (CDCl$_3$ 300 MHz) δ1.24 (d, 18H), 2.72 (m, 2H), 3.38 (br, 3H), 3.59 (br, 3H), 4.02 (br, 2H), 5.04 (br, 1H), 6.61 (d, 2H), 6.88 (d, 2H), 6.97 (m 3H), 7.26 (d, 2H).

Step d) (1S)-2-((tert-Butoxycarbonyl){4-[(2,2,2-trifluoroacetyl)amino]phenethyl}amino)-1-(phenoxymethyl)ethyl tert-butyl carbonate A mixture of compound from(1S)-2-[(4-aminophenethyl) (tert-butoxycarbonyl)amino]-1-(phenoxymethyl)ethyl tert-butyl carbonate (2.90 g, 5.95 mmol), S-ethyl-trifluorothioacetate (2.38 ml, 18.44 mmol) and methanol (21 mL) was stirred at ambient temperature for 18 hours. Evaporation and purification by flash chromatography (hexanes/ ethyl acetate/methanol 7/2.5/0.5) to give a white solid (62% yield): MS m/e 581 (M–H)$^+$; $^1$H NMR (DMSO-d$_6$ 300 MHz) δ1.47 (s, 18H), 2.86 (m, 2H), 3.32 (br, 1H), 3.45 (br, 2H), 3.46 (br, 1H), 4.02 (br, 2H), 5.11 (br, 1H), 6.88 (d, 2H), 6.97 (t, 1H), 7.22 (m, 4H), 7.48 (d, 2H), 7.80 (s, 1H)

Analysis for C$_{29}$H$_{37}$F$_3$N$_2$O$_7$ Calc'd: C, 59.78; H, 6.40; N, 4.81. Found: C, 59.49; H, 6.42; N, 4.61.

Step e) (1S)-2-((tert-Butoxycarbonyl){4-[methyl(2,2,2-trifluoroacetyl)amino]phenethyl}amino)-1-(phenoxymethyl)ethyl tert-butyl carbonate This compound was prepared from (1S)-2-((tert-butoxycarbonyl){4-[(2,2,2-trifluoroacetyl)amino] phenethyl}amino)-1-(phenoxymethyl)ethyl tert-butyl carbonate and methyl iodide as described in example 1, srep a, and was obtained as a colorless oil. MS m/e 596 M)$^+$; $^1$H NMR (t300 MHz) δ1.48 (s, 18H), 2.93 (br, 2H), 3.30 (m, 1H), 3.34 s, 3H), 3.50 (m, 3H), 4.10 (br, 2H), 4.05 (m, 1H), 5.15 (b 6.90 (d, 2H), 7.15 (t, 1H), 7.25 (d, 2H), 7.28 (m, 4H).

Step f) (1S)-2-{(tert-Butoxycarbonyl)[4-(methylamino) phenethyl]amino}-1-(phenoxymethyl)ethyl tert-butyl carbonate A mixture of (1S)-2-((tert-butoxycarbonyl){4-[methyl(2, 2,2-trifluoroacetyl)amino]phenethyl)amino)-1-(phenoxymethyl)ethyl tert-butyl carbonate (2.1 g, 3.52 mmol), 40% aqueous solution of potassium hydroxide (15 mL) and dioxane (10 mL) was stirred at ambient temperature for 18 hours. The product was extracted with dichloromethane, and dried over K$_2$CO$_3$. Evaporation and purification by flash chromatography (hexanes/ dichloromethane/methanol (9/0.7/0.3) gave a light yellow oil (1.62 g, 92% yield): MS m/e 500 M$^+$; $^1$H NMR (CDCl$_3$ 300 MHz), δ1.48 (s, 18H), 2.93 (br, 2H), 3.30 (m, 1H), 3.34 s, 3H), 3.50 (m, 3H), 4.05 (m, 1H), 4.10 (br, 2H),5.15 (br, 1H), 6.56 (d, 2H), 6.86 (d, 2H), 6.99 (m, 4H), 7.02 (m, 4H).

Step g) (1S)-2-((tert-Butoxycarbonyl){4-[(2,4-dioxo-1,3-thiazolidin-5-yl)(methyl)amino]phenethyl}amino)-1-(phenoxymethyl)ethyl tert-butyl carbonate This compound was prepared from (1S)-2-{(tert-butoxycarbonyl)[4-(methylamino)phenethyl]amino}-1-(phenoxymethyl)ethyl tert-butyl carbonate and 5-bromo-1, 3-thiazolidine-2,4-dione in substantially the same manner as described in example 1, step d, and was obtained as an off white solid (50% yield): MS m/e 616 (M+)$^+$; $^1$H NMR (DMSO-d$_6$ 300 MHz) δ1.38 (s, 18H), 2.67 (t, 2H), 2.74 (s, 3H), 3.29 (m, 2H), 3.42 (m, 2H), 4.01 (m, 1H), 4.02 (m, 1H), 5.02 (br, 1H), 6.90 (m, 6H), 7.07 (d, 2H), 7.28 (t, 2H), 12.61 (s, 1H);

Analysis for C$_{31}$H$_{41}$N$_3$O$_8$ S Calc'd: C, 60.47; H, 6.71; N, 6.82. Found: C, 59.23; H, 6.60; N, 6.38.

Step h) 5-[4-(2-{[(2S)-2-Hydroxy-3-phenoxypropyl] amino}ethyl)(methyl)anilino]-1,3-thiazolidine-2,4-dione This compound was prepared from (1S)-2-((tert-butoxycarbonyl){4-[(2,4-dioxo-1,3-thiazolidin-5-yl) (methyl)amino]phenethyl}amino)-1-(phenoxymethyl)ethyl tert-butyl carbonate and trifluoroacetic acid in substantially the same manner as described in example 1, step e, and was obtained as a white solid (31% yield): mp 58° C.; MS m/e 416 (M+H)$^+$; $^1$H NMR (DMSO-d$_6$ 300 MHz) δ2.76 (m, 3H), 2.88 (m, 2H), 3.03 (m, 1H), 3.22 (m, 2H), 3.90 (m, 2H), 4.41 (br, 1H), 5.88 (br, 1H), 6.94 (m, 6H), 7.16 (d, 2H), 7.29 (d, 2H), 8.64 (s, 2H), 12.36 (s, 1H);

Analysis for C$_{17}$H$_{18}$F$_3$N$_2$O$_3$S×1.3 CF$_3$COOH×1 H$_2$O Calc'd: C, 48.68; H, 4.52; N, 7.22. Found: C, 48.93; H 4.59; N, 7.33.

EXAMPLE 18

5-[4-(2-{[(2R)-2-(3-Chlorophenyl)-2-hydroxyethyl] amino}propyl)anilino]-1,3-thiazolidine-2,4-dione Step a) (1R)-2-{[2-(4-Aminophenyl)-1-methylethyl] amino}-1-(3-chlorophenyl)-1-ethanol This compound was prepared from (2R)-2-(3-chlorophenyl)oxirane and 2-(4-aminophenyl)-1-methylethylamine as described in example 1, step b, with one modification, the mixture was stirred in tetrahydrofuran at 70° C. for 48 hours. The product was triturated ethyl ether to give a white solid (48% yield): MS m/e 305 (M+H)$^+$; $^1$H NMR (DMSO-d$_6$ 300 MHz) δ0.86 (m, 3H),2.23 (m, 1H), 2.53 (m, 2H), 2.66 (m, 2H),4.58 (m, 1H), 5.30 (d, 2H), 5.40 (br, 1H), 6.45 (m, 2H), 6.77 (m, 2H), 7.26(m, 4H).

Step b) tert-butyl 2-(4-Aminophenyl)-1-methylethyl[(2R)-2-(3-chlorophenyl)-2-hydroxyethyl]carbamate This compound was prepared from 1R)-2-{[2-(4-aminophenyl)-1-methylethyl]amino}-1-(3-chlorophenyl)-1-ethanol and di-tert-butyl dicarbonate in substantially the same manner as described in example 1, step c, and was obtained as a colorless oil (68% yield): MS m/e 405 M$^+$.

Step c) tert-Butyl (2R)-2-(3-chlorophenyl)-2-hydroxyethyl (2-{4-[(2,4-dioxo-1,3-thiazolidin-5-yl)amino]phenyl}-1-methyl ethyl)carbamate This compound was prepared from tert-butyl 2-(4-aminophenyl)-1-methylethyl[(2R)-2-(3-chlorophenyl)-2-hydroxyethyl]carbamate and 5-bromo-1,3-thiazolidine-2,4-dione in substantially the same manner as described in example 1, step d, and was obtained as a yellow solid (82% yield): MS m/e 520/522 (M+H)$^+$;

Analysis for C$_{25}$H$_{30}$ClN$_3$O$_5$ S Calc'd: C, 57.74; H, 5.81; N, 8.08. Found: C, 57.06; H, 5.88; N, 7.99.

Step d) 5-[4-(2-{[(2R)-2-(3-Chlorophenyl)-2-hydroxyethyl] amino}propyl)anilino]-1,3-thiazolidine-2,4-dione This compound was prepared from tert-butyl (2R)-2-(3-chlorophenyl)-2-hydroxyethyl(2-{4-[(2,4-dioxo-1,3-thiazolidin-5-yl)amino]phenyl}-1-methylethyl)carbamate and trifluoroacetic acid in substantially the same manner as described in example 1, step e, and was obtained as a white solid (21% yield): mp 83–85°; MS m/e 420/422 (M+H)$^+$; $^1$H NMR (DMSO-d$_6$ 300 MHz) δ1.12 (t, 3H), 3.07 (m, 3H), 4.01 (br, 1H), (m, 2H), 4.93 (t, H), 6.49 (d, 1H), 6.63 (m, 2H), 7.06 (m, 3H), 7.43 (m, 3H), 7.44 (s, 1H), 8.73 (br, 2H), 12.22 (s, 1H);

Analysis for C$_{20}$H$_{22}$ClN$_3$O$_3$S×1.8 CF$_3$COOH×0.46 H$_2$O Calc'd: C, 44.70; H, 3.90; N, 6.62. Found: C, 44.60; H, 3.79; N, 6.58.

EXAMPLE 19

5-{4-[2-({(2R)-2-Hydroxy-3-[(2-oxo-2,3-dihydro-1H-benzimidazol-4-yl)oxy]propyl}amino)ethyl]anilino}-1,3-thiazolidine-2,4-dione Step a) 2-Nitro-6-[(2R)-oxiranylmethoxy]aniline A mixture of 2-amino-3-nitrophenol (25.3 g, 164.1 mmol), (2S)-(+)oxiranylmethyl 3-nitrobenzenesulfonate (42.5, 164.1 mmol), potassium carbonate (29 g, 209.8 mmol) and acetone (300 mL) was refluxed for 6 hours. After cooling to room temperature, the mixture was filtered, and the filtrate was removed in vacuo. The residue was partitioned between dichloromethane and water. The organic layer was washed with aqueous bicarbonate, and dried over $MgSO_4$. Evaporation and purification by recrystallization from dichloromethane/hexanes gave an orange colored solid (31 g, 90% yield): MS m/e 210 (M)$^+$;

Analysis for $C_9H_{10}N_2O_4$ Calc'd: C, 51.43; H, 4.80; N, 13.33. Found: C, 50.92; H, 4.57; N, 13.41.

Step b) (2R)-1-(2-Amino-3-nitrophenoxy)-3-[(4-aminophenethyl)amino]-2-propanol

This compound was prepared from 2-nitro-6-[(2R)oxiranylmethoxy]aniline and 4-(2-aminoethyl)aniline as described in example 1, step b, with one modification, the mixture was stirred in tetrahydrofuran at 70° C. for 24 hours, and the product was triturated with dichloromethane to give a yellow solid (63% yield): MS m/e 346 (M)$^+$; $^1$H NMR (DMSO-$d_6$ 300 MHz) δ1.87 (br 1H), 2.50 (m, 2H), 2.67 (m, 4H), 3.82 (m, 1H), 3.84 (m, 1H), 4.01 (m, 1H), 4.81 (s, 2H), 5.24 (s, 1H), 6.46 (d, 2H), 6.59 (m, 1H), 6.86 (d, 2H), 7.02 (d, 1H), 7.22 (s, 2H), 7.59 (d, 1H);

Analysis for $C_{17}H_{22}N_4O_4$ Calc'd: C, 58.95; H, 6.4; N, 16.17. Found: C, 58.30; H, 7.15; N, 15.61.

Step c) tert-Butyl (2R)-3-(2-amino-3-nitrophenoxy)-2-hydroxypropyl(4-aminophenethyl)carbamate This compound was prepared from (2R)-1-(2-amino-3-nitrophenoxy)-3-[(4-aminophenethyl)amino]-2-propanol and di-tert-butyl dicarbonate as described in example 1, step c, to give a yellow solid (77% yield): MS m/e 447 (M)$^+$; $^1$H NMR (DMSO-$d_6$ 300 MHz) δ1.36 (s 9H), 2.59 (m, 2H), 3.24 (m, 4H), 3.79 (m, 1H), 4.00 (m, 2H), 4.81 (s, 2H), 5.35 (d, 1H), 6.46 (d, 2H), 6.55 (t, 1H), 6.81 (d, 2H), 7.00 (d, 1H), 7.21 (s, 2H), 7.57 (d, 1H);

Analysis for $C_{22}H_{30}N_4O_5$ Calc'd: C, 59.18; H, 6.77; N, 12.55. Found: C, 59.32; H, 6.65; N, 12.81.

Step d) tert-Butyl 4-aminophenethyl[(2R)-3-(2,3-diaminophenoxy)-2-hydroxypropyl]carbamate This compound was prepared from tert-butyl (2R)-3-(2-amino-3-nitrophenoxy)-2-hydroxypropyl(4-aminophenethyl)carbamate as described in EP 0764640 to give a yellow solid (70% yield): MS m/e 417 (M)$^+$; $^1$H NMR (DMSO-$d_6$ 300 MHz) δ1.37 (s 9H), 2.57 (m, 2H), 3.06 (m, 1H), 3.30 (m, 3H), 3.63 (m, 1H), 3.68 (m, 1H), 3.98 (m, 1H), 4.16 (br, 2H), 4.45 (br, 2H), 4.82 (br, 2H), 5.13 (d, 1H), 6.11 (d, 1H), 6.19 (d, 1H), 6.32 (t, 1H), 6.45 (d, 2H), 6.79 (d, 2H);

Analysis for $C_{22}H_{32}N_4O_4$ Calc'd: C, 63.44; H, 7.74; N, 13.45. Found: C, 62.17; H, 7.53; N, 13.25.

Step d) tert-Butyl 4-aminophenethyl{(2R)-2-hydroxy-3-[(2-oxo-2,3-dihydro-1H-benzimidazol-4-yl)oxy]propyl}carbamate A mixture of tert-butyl 4-aminophenethyl[(2R)-3-(2,3-diaminophenoxy)-2-hydroxypropyl]carbamate (1.0 g, 2.4 mmol), 1,1-carbonyldiimidazole (0.52 g, 3.2 mmol) and dioxane (20 mL) was stirred at ambient temperature for 18 hours. The solvent was removed in vacuo and the residue was purified by flash chromatography (hexanes/dichloromethane/ethanol 4/4/2) to give an off white solid (0.28 g, 26% yield): MS m/e 443 (M+H)$^+$; $^1$H NMR (DMSO-$d_6$ 300 MHz) δ1.37 (s 9H), 2.59 (m, 2H), 3.31 (m, 3H), 3.40 (m, 1H), 3.85 (m, 1H), 3.97 (d, 2H), 4.82 (s, 2H), 4.94 (d, 1H), 6.43 (d, 2H), 6.77 (d, 2H), 6.82 (m, 3H), 10.55 (s, 1H), 10.61 (s, 1H).

Step e) tert-Butyl 4-[(2,4-dioxo-1,3-thiazolidin-5-yl)amino] phenethyl{(2R)-2-hydroxy-3-[(2-oxo-2,3-dihydro-1H-benzimidazol-4-yl)oxy]propyl}carbamate This compound was prepared from tert-butyl 4-aminophenethyl{(2R)-2-hydroxy-3-[(2-oxo-2,3-dihydro-1H-benzimidazol-4-yl)oxy]propyl}carbamate and 5-bromo-1,3-thiazolidine-2,4-dione in substantially the same manner as described in example 1, step d, and was obtained as a yellow solid (31% yield): MS m/e 558 (M+H)$^+$; $^1$H NMR (DMSO-$d_6$ 300 MHz) δ1.31 (s 9H), 2.64 (m, 2H), 3.41 (m, 5H), 3.84 (m, 1H), 3.96 (m, 2H), 4.92 (m, 1H), 6.45 (m, 1H), 6.56 (m, 3H), 6.81 (m, 2H), 6.97 (m, 2H), 10.55 (s, 1H), 10.59 (s, 1H), 12.25 (br, 1H).

Step f) 5-{4-[2-({(2R)-2-Hydroxy-3-[(2-oxo-2,3-dihydro-1H-benzimidazol-4-yl)oxy]propyl}amino)ethyl]anilino}-1,3-thiazolidine-2,4-dione This compound was prepared from tert-butyl 4-[(2,4-dioxo-1,3-thiazolidin-5-yl)amino]phenethyl{(2R)-2-hydroxy-3-[(2-oxo-2,3-dihydro-1H-benzimidazol-4-yl)oxy] propyl}carbamate and trifluoroacetic acid in substantially the same manner as described in example 1, step e, and was obtained as a light yellow solid (38% yield): mp 172° C.; MS m/e 458 (M+H)$^+$; $^1$H NMR (DMSO-$d_6$ 300 MHz) δ2.90 (m, 2H), 3.22 (m, 4H), 3.98 (m, 1H), 4.05 (m, 1H), 4.06 (m, 1H), 5.74 (d, 1H), 6.50 (d, 1H), 6.60 (m, 4H), 6.86 (t, 1H), 7.10 (m, 3H), 8.56 (s, 2H), 10.60 (s, 1H), 10.63 (s, 1H), 12.19 (s, 1H);

Analysis for $C_{21}H_{23}N_5O_5S \times 1$ $CF_3COOH$ Calc'd: C, 48.34; H, 4.23; N, 12.25. Found: C, 47.79; H, 4.48; N, 11.20.

EXAMPLE 20

5-{[2-({[(2R)-2-(3-Chlorophenyl)-2-hydroxyethyl]amino}methyl)-1-benzofuran-5-yl]amino}-1,3-thiazolidine-2,4-dione Step a) 2-(Bromomethyl)-6-nitro-1-benzofuran Acetoxime (50 g, 355 mmol) was added portionwise into a mixture of sodium hydride (60% in mineral oil, 15.52 g, 390.5 mmol) and N,N-dimethylformamide. The mixture was stirred for 1 hour. During this period the mixture was allowed to come to room temperature. The mixture was cooled to 0° C., and 4-fluoro-nitrobenzene 92702 g, 372.7 mmol) was added slowly. The new mixture was stirred at 0° C. for 2 hours and then was stirred at room temperature for 16 hours. The reaction mixture was quenched with brine and the precipitated solid filtered and dried to give an off-white solid (66 g). This product was taken in ethanol (1000 mL) and anhydrous hydrochloric acid was passed through the mixture for 2 hours. The mixture was then refluxed for 20 hours and the volatiles were removed in vacuo. The residue was taken in water and the precipitated solid filtered and dried to give an off-white solid (50.6 g). This product was taken in carbon tetrachloride and 1,3-dibromo-5,5-dimethylhydantoin (40.4 g, 141.2 mmol) and benzoyl peroxide were added into the mixture. The mixture was then refluxed under UV light for 6 hours. The volatiles were removed in vacuo and the residue was taken in ethyl acetate and washed with water and brine. The organic extracts were dried over $MgSO_4$. Evaporation and crystallization form ethyl ether/hexanes gave a white solid (59.6 g): $^1$H NMR (DMSO-$d_6$ 300 MHz) δ5.0 (s, 2H), 7.24 (s, 1H), 7.83 (m, 1H), 8.24 (m, 1H), 8.63 (m, 1H).

Step b) (6-Nitro-1-benzofuran-2-yl)methanamine

A mixture of 2-(bromomethyl)-6-nitro-1-benzofuran (44.0 g, 171.9 mmol), potassium phthalimide (47.7 mmol), acetonitrile (1000 mL), and 18-C-6 (4.5 g, 17.19 mmol) was stirred at room temperature for 10 hours. The volatiles were removed in vacuo, and the residue was taken in ethyl acetate and washed with water. The organic extracts were dried over $MgSO_4$. Evaporation and crystallization form ethyl ether/hexanes gave an off-white solid (53.2 g).

This product was taken in ethanol and hydrazine (7.2 mL, 233 mmol) was added. The mixture was refluxed for 5 hours and the volatiles were removed in vacuo. The residue was acidified with hydrochloric acid, and the precipitated solids were filtered off and discarded. The filtrate was basified with sodium hydroxide (10 N) and extracted with ethyl acetate. The organic extracts were dried over $MgSO_4$. Evaporation and crystallization form ethyl ether/hexanes gave a brownish solid (24.6 g): MS m/e 192 $M^+$;

Analysis for $C_9H_8N_2O_3$ Calc'd: C, 56.25; H, 4.20; N, 14.58. Found: C, 56.21; H, 4.13; N, 14.41.

Step c) (1R)-1-(3-chlorophenyl)-2-{[(5-nitro-1-benzofuran-2-yl)methyl]amino}-1-ethanol This compound was prepared from (R)-(+)-3-chlorostyrene oxide and (6-nitro-1-benzofuran-2-yl) methanamine as described in example 1, step b, to give a yellow solid (67% yield), MS m/e 347 $(M+H)^+$; Analysis for $C_{17}H_{15}ClN_2O_4$ Calc'd: C, 58.88; H, 4.36; N, 8.08. Found: C, 58.75; H, 4.36; N, 8.01.

Step d) tert-Butyl (2R)-2-(3-chlorophenyl)-2-hydroxyethyl [(5-nitro-1-benzofuran-2-yl)methyl]carbamate This compound was prepared from (1 R)-1-(3-chlorophenyl)-2-{[(5-nitro-1-benzofuran-2-yl)methyl] amino}-1-ethanol and di-tert-butyl dicarbonate as described in example 1, step c, to give a tan solid (91% yield), MS m/e 447 $(M+H)^+$.

Step e) tert-Butyl (5-amino-1-benzofuran-2-yl)methyl[(2R)-2-(3-chlorophenyl)-2-hydroxyethyl]carbamate A solution of tert-butyl (2R)-2-(3-chlorophenyl)-2-hydroxyethyl[(5-nitro-1-benzofuran-2-yl)methyl]carbamate (2.95 g, 6.60 mmol) in methyl alcohol (30 mL) was added over 10 minutes into a slurry of iron (1.76 g, 33 mmol) and 0.025 M aqueous ammonium chloride (33 mL). The reaction mixture was warmed up at reflux for 4 hours. The mixture was then filtered through celite and washed with hot methyl alcohol. The volatiles were removed in vacuo and the residue was neutralized with saturated aqueous bicarbonate, and extracted with dichloromethane. The organic extracts were dried over $MgSO_4$. Evaporation and purification by recrystallization from dichloromethane and hexanes gave a tan solid (1.80 g, 65% yield): MS m/e 417 $(M+H)^+$; $^1H$ NMR (DMSO-$d_6$ 300 MHz) $\delta$1.34 (s 9H), 3.27 (m, 1H), 3.45 (m, 1H), 4.57 (m, 2H), 4.82 (m, 3H), 5.69 (m, 1H), 6.52 (m, 2H), 6.66 (s, 1H), 7.18 (t, 1H), 7.31 (m, 4H).

Step f) tert-Butyl (2R)-2-(3-chlorophenyl)-2-hydroxyethyl ({5-[(2,4-dioxo-1,3-thiazolidin-5-yl)amino]-1-benzofuran-2-yl}methyl)carbamate This compound was prepared from tert-butyl (5-amino-1-benzofuran-2-yl)methyl[(2R)-2-(3-chlorophenyl)-2-hydroxyethyl]carbamate and 5-bromo-1,3-thiazolidine-2,4-dione in substantially the same manner as described in example 1, step d, and was obtained as a yellow solid (75% yield), MS m/e 530 $(M-H)^+$; $^1H$ NMR (DMSO-$d_6$ 300 MHz) $\delta$1.28 (s 9H), 3.24 (m, 1H), 3.40 (m, 1H), 4.54 (m, 2H), 4.81 (br, 1H), 5.66 (br, 1H), 6.47 (m, 1H), 6.61 (d, 1H), 6.65 (d, 1H), 6.78 (s, 1H), 6.96 (d, 1H), 7.28 (m, 5H), 12.16 (s, 1H).

Step g) 5-{[2-({[(2R)-2-(3-Chlorophenyl)-2-hydroxyethyl]amino}methyl)-1-benzofuran-5-yl]amino}-1,3-thiazolidine-2,4-dione This compound was prepared from tert-butyl (2R)-2-(3-chlorophenyl)-2-hydroxyethyl({5-[(2,4-dioxo-1,3-thiazolidin-5-yl)amino]-1-benzofuran-2-yl}methyl) carbamate and trifluoroacetic acid in substantially the same manner as described in example 1, step e, and was obtained as a light yellow solid (60% yield): mp 70° C.; MS m/e 458 $(M+H)^+$; $^1H$ NMR (DMSO-$d_6$ 300 MHz) $\delta$3.08 (m, 1H), 3.20 (m, 1H), 4.42 (m, 2H), 4.94 (d, 1H), 6.28 (d, 1H), 6.50 (d, 1H), 6.78 (d, 1H), 6.86 (s, 1H), 6.97 (s, 1H), 7.05 (d, 1H), 7.34 (m, 5H), 9.38 (br, 2H), 11.55 (br, 1H);

Analysis for $C_{20}H_{18}ClN_3O_4S\times1$ $CF_3COOH\times0.28$ $H_2O$ Calc'd: C, 47.90; H, 3.44; N, 7.62 Found: C, 46.84; H, 3.46; N, 7.12.

EXAMPLE 21

5-(4-{2-[(2S)-2-Hydroxy-3-(naphthalen-2-yloxy)-propylamino]-ethyl}-phenylamino)-thiazolidine-2,4-dione Step a) 2-[(2-Naphthyloxy)methyl]oxirane NaH (60% in mineral oil, 2.16 g, 54.0 mmol) was added portionwise to 50 mL of DMF with stirring at room temperature under a nitrogen atmosphere. A solution of 2-naphthol (6.74 g, 46.28 mmol) in DMF (50 mL) was then added dropwise to this suspension over a period of 0.5 hour. After stirring for 1 hour a solution of (2S)-oxazolylmethyl 3-nitrobenzenesulfonate (10 g, 38.57 mmol) in DMF (50 mL) was added dropwise into this mixture over a period of 15 min. The mixture was then stirred at room temperature overnight. The reaction was quenched with aqueous ammonium chloride to pH 5 and further diluted with water. The formed solid was isolated by filtration to give (6.14 g, 80% yield): mp: 72–73° C.; MS m/z 200 $M^+$;

Analysis for $C_{13}H_{12}O_2$ Calc'd: C, 77.98; H, 6.04; N, 0.00; Found: C, 78.12; H, 6.63; N, 0.12.

Step b) (2S)-1-[(4-Aminophenethyl)amino]-3-(2-naphthyloxy)-2-propanol

A mixture of 2-[(2-naphthyloxy)methyl]oxirane (3.0 g, 15.0 mmol), and 2-(4-aminophenyl)ethylamine (6.1 mL, 45.0 mmol) in THF (20 mL) was stirred at room temperature under a nitrogen atmosphere overnight. The solvent was removed in vacuo and the residue was stirred in ethyl ether (4×150 mL) overnight. The solid was isolated by filtration to give an off-white solid (2.9 g, 58% yield): mp: 112–113° C.; MS m/z 336 $M^+$; Analysis for $C_{21}H_{24}N_2O_2$ Calc'd: C, 74.97; H, 7.19; N, 8.33; Found: C, 75.16; H, 7.18; N, 8.48.

Step c) 5-(4-{2-[(2S)-2-Hydroxy-3-(naphthalen-2-yloxy)-propylamino]-ethyl}-phenylamino)-thiazolidine-2,4-dione A mixture of (2S)-1-[(4-aminophenethyl)amino]-3-(2-naphthyloxy)-2-propanol (2.86 g, 8.5 mmol), N,N-diisopropylethylamine (3.7 mL, 21.2 mmol) and di-tert-butyl dicarbonate (2.25 g, 10.2 mmol) in THF (55 mL) was stirred at room temperature under a nitrogen atmosphere for 3 hours. The reaction was quenched with saturated aqueous sodium bicarbonate and further diluted with water. The aqueous layer was extracted with ethyl acetate. The extract was washed with water, and dried with $MgSO_4$. Concentration and purification by flash column chromatography (hexanes/ethyl acetate 1/1) gave a white solid (2.34 g, 63% yield). A mixture of this product (2.3 g, 5.27 mmol), triethylamine (0.96 mL, 6.85 mmol) and 5-bromodiazolidine-2,4-dione (1.34 g, 6.85 mmol) in DMF (20 mL) was stirred at room temperature under a nitrogen atmosphere for 7 hours. The mixture was diluted with water and extracted with methylene chloride. The extract was washed with water, and dried with $MgSO_4$. Evaporation and purification by flash column chromatography (methylene chloride/methanol 95/5) gave a solid (2.15 g, 70% yield). A solution of this product (2.1 g, 3.8 mmol), trifluoroacetic acid (14 mL) and methylene chloride (20 mL) was stirred at room temperature under a nitrogen atmosphere for 30 min. The reaction mixture was concentrated to give an off-white solid (1.88 g, 77% yield): mp: 90–91° C.; MS m/z 452 (M+H)$^+$; Analysis for $C_{24}H_{25}N_3O_4S \times 1.3\ H_2O \times 1.0\ CF3CO_2H$ Calc'd: C, 53.02; H, 4.89; N, 7.13; Found: C, 53.28; H, 4.41; N, 6.88.

EXAMPLE 22

5-(4-{2-[(2S)-3-(Biphenyl-4-yloxy)-2-hydroxy-propylamino]-ethyl}-phenylamino)-thiazolidine-2,4-dione Step a) 2-[([1,1'-Biphenyl]-4-yloxy)methyl]oxirane The title compound was prepared from 4-phenylphenol and (2S)-oxiranylmethyl 3-nitrobenzenesulfonate in substantially the same manner as described in example 21, step a. The product was obtained as a white solid: mp: 91–92° C.; MS m/z 226 M$^+$;

Analysis for $C_{15}H_{14}O_2$ Calc'd: C, 79.62; H, 6.24; N, 0.00; Found: C, 79.35; H, 6.36; N, –0.03.

Step b) (2S)-1-[(4-Aminophenethyl)amino]-3-([1,1'-biphenyl]-4-yloxy)-2-propanol

The title compound was prepared from 2-[([1,1'-biphenyl]-4-yloxy)methyl]oxirane, and 2-(4-aminophenyl)ethylamine in substantially the same manner, as described in example 21, step b. The product was obtained as a white solid: 118–119° C.; MS m/z 362 M$^+$; Analysis for $C_{23}H_{26}N_2O_2$ Calc'd: C, 76.21; H, 7.23; N, 7.73; Found: C, 75.83; H, 7.24; N, 7.58.

Step c) 5-(4-{2-[(2S)-3-(Biphenyl-4-yloxy)-2-hydroxy-propylamino]-ethyl}-phenylamino)-thiazolidine-2,4-dione The title compound was prepared from (2S)-1-[(4-aminophenethyl)amino]-3-([1,1'-biphenyl]-4-yloxy)-2-propanol, and 5-bromodiazolidine-2,4-dione in substantially the same manner, as described in example 21, step c. The product was obtained as a white solid: mp: 70–71° C.; MS m/z 478 (M+H)$^+$; Analysis for $C_{26}H_{27}N_3O_4S \times 0.36\ DMF \times 2.0\ F_3CCO_2H$ Calc'd: C, 49.54; H, 4.54; N, 6.25; Found: C, 49.56; H, 4.27; N, 6.22.

EXAMPLE 23

5-(4-{2-[2-Hydroxy-3-(naphthalen-1-yloxy)-propylamino]-ethyl}-phenylamino)-thiazolidine-2,4-dione Step a) 2-[(1-Naphthyloxy)methyl]oxirane The title compound was prepared from 1-naphthol and (2S)-oxiranylmethyl 3-nitrobenzenesulfonate in substantially the same manner as described in example 21, step a. The product was obtained as an oil: MS m/z 200 M$^+$.

Step b) (2S)-1-[(4-Aminophenethyl)amino]-3-(1-naphthyloxy)-2-propanol

The title compound was prepared from 2-[(1-naphthyloxy)methyl]oxirane, and 2-(4-aminophenyl)ethylamine in substantially the same manner, as described in example 21, step b. The product was obtained as a light yellow sticky solid: 107–108° C.; MS m/z 337 (M+H)$^+$; Analysis for $C_{21}H_{24}N_2O_2$ Calc'd: C, 74.97; H, 7.19; N, 8.33; Found: C, 74.56; H, 7.36; N, 8.49.

Step c) 5-(4-{2-[2-Hydroxy-3-(naphthalen-1-yloxy)-propylamino]-ethyl}-phenylamino)-thiazolidine-2,4-dione The title compound was prepared from (2S)-1-[(4-aminophenethyl)amino]-3-(1-naphthyloxy)-2-propanol, and 5-bromodiazolidine-2,4-dione in substantially the same manner, as described in example 21, step c. The product was obtained as an off-white solid: mp: 61–62° C.; MS m/z 452 (M+H)$^+$; Analysis for $C_{23}H_{27}N_4O_4S\ Na \times 1.6\ H_2O \times 1.5\ CF_3CO_2H$ Calc'd: C, 49.79; H, 4.60; N, 6.45; Found: C, 50.16; H, 4.22; N, 6.08.

EXAMPLE 24

5-(4-{2-[(2S)-3-(Benzo[1,3]dioxol-5-yloxy)-2-hydroxy-propylamino]-ethyl}-phenylamino)-thiazolidine-2,4-dione Step a) 5-(2-Oxiranylmethoxy)-1,3-benzodioxole The title compound was prepared from 3,4-methylenedioxyphenol and (2S)-oxiranylmethyl 3-nitrobenzenesulfonate in substantially the same manner as described in example 21, step a. The product was obtained as an oil: MS m/z 124 M$^+$; Analysis for $C_{15}H_{14}O_2$ Calc'd: C, 61.85; H, 5.19; N, 0.00; Found: C, 61.53; H, 5.22; N, 0.14.

Step b) (2S)-1-[(4-Aminophenethyl)amino]-3-(1,3-benzodioxol-5-yloxy)-2-propanol

The title compound was prepared from 5-(2-oxiranylmethoxy)-1,3-benzodioxole and 2-(4-aminophenyl)ethylamine in substantially the same manner, as described in example 21, step b. The product was obtained as a solid: 96–97° C.; MS m/z 331 (M+H)$^+$; Analysis for $C_{18}H_{22}N_2O_4$ Calc'd: C, 65.44; H, 6.71; N, 8.48; Found: C, 65.26; H, 6.63; N, 8.52.

Step c) 5-(4-{2-[(2S)-3-(Benzo[1,3]dioxol-5-yloxy)-2-hydroxy-propylamino]-ethyl}-phenylamino)-thiazolidine-2,4-dione The title compound was prepared from (2S)-1-[(4-aminophenethyl)amino]-3-(1,3-benzodioxol-5-yloxy)-2-propanol, and 5-bromodiazolidine-2,4-dione in substantially the same manner, as described in example 21, step c. The product was obtained as an off-white solid: mp: 65° C. (decomposed); MS m/z 446 (M+H)$^+$; Analysis for $C_{21}H_{23}N_3O_6S \times 0.87\ H_2O \times 1.0\ CF_3CO_2H$ Calc'd: C, 48.31; H, 4.66; N, C, 48.51; H, 4.49; N, 7.08.

EXAMPLE 25

5-[(4-{2-[(2S)-3-(4-Benzyloxy-phenoxy)-2-hydroxy-propylamino]-ethyl}-phenyl)-(4-bromo-benzyl)-amino]-thiazolidine-2,4-dione Step a) tert-Butyl (2S)-3-[4-(benzyloxy)phenoxy]-2-hydroxypropyl{4-[(4-bromobenzyl)amino]phenethyl}carbamate A mixture of tert-butyl 4-aminophenethyl{(2S)-3-[4-(benzyloxy)phenoxy]-2-hydroxypropyl}carbamate (0.20 g, 0.41 mmol), 4-bromobenzyl bromide (0.16 g, 0.62 mmol) and potassium carbonate (0.08 g, 0.62 mmol) in acetone (2.2 mL) was stirred at room temperature for two days. The mixture was diluted with water and extracted with ethyl acetate. The extract was washed with water and dried with $MgSO_4$. Evaporation and purification by flash column chromatography (hexane/ethyl acetate 7/3) gave a white solid (0.06 g, 21%): MS m/z 661 [M+H]$^+$.

Step b) 5-[(4-{2-[(2S)-3-(4-Benzyloxy-phenoxy)-2-hydroxy-propylamino]-ethyl}-phenyl)-(4-bromo-benzyl)-amino]-thiazolidine-2,4-dione The title compound was prepared from tert-butyl (2S)-3-[4-(benzyloxy)phenoxy]-2-hydroxypropyl{4-[(4-bromobenzyl)amino]phenethyl}carbamate, and 5-bromodiazolidine-2,4-dione in substantially the same manner, as described in example 4. The product was obtained as a light yellow solid: mp: 50–52° C.; MS m/z 676 [M+H]$^+$; Analysis for $C_{34}H_{34}BrN_3O_5S \times 1.6\ CF_3CO_2H$ Calc'd: C, 52.01; H, 4.18 N, 4.89; Found: C, 51.73; H, 4.27; N, 4.57.

EXAMPLE 26

5-[(4-{2-[(2S)-3-(4-Benzyloxy-phenoxy)-2-hydroxy-propylamino]-ethyl}-phenyl)-methyl-]-thiazolidine-2,4-dione Step a) tert-Butyl (2S)-3-[4-(benzyloxy)phenoxy]-2-hydroxypropyl[4-(methylamino) phenethyl]carbamate The title compound was prepared from tert-butyl 4-aminophenethyl{(2S)-3-[4-(benzyloxy)phenoxy]-2-hydroxypropyl]carbamate and iodomethane in substantially the same manner, as described in example 25, step a. The product was obtained as an oil. MS m/z 507 [M+H]$^+$.

Step b) 5-[(4-{2-[(2S)-3-(4-Benzyloxy-phenoxy)-2-hydroxy-propylamino]-ethyl}-phenyl)-methyl-amino]-thiazolidine-2,4-dione The title compound was prepared from tert-butyl (2S)-3-[4-(benzyloxy)phenoxy]-2-hydroxypropyl[4-(methylamino) phenethyl]carbamate, and 5-bromodiazolidine-2,4-dione in substantially the same manner, as described in example 4. The product was obtained as an off-white solid; mp: 51–53° C.; MS m/z 522 (M+H)$^+$; Analysis for $C_{28}H_{31}N_3O_5S \times 1.0$ $CF_3CO_2H$ Calc'd: C, 56.69; H, 5.07; N, 6.61; Found: C, 57.66; H, 4.57; N, 6.10.

EXAMPLE 27

5-[(4-{2-[(2S)-3-(4-Benzyloxy-phenoxy)-2-hydroxy-propylamino]-ethyl}-phenyl)-[3-(4-fluoro-phenyl)-prop-2-ynyl]-amino}-thiazolidine-2,4-dione
Step a) tert-Butyl (2S)-3-[4-(benzyloxy)phenoxy]-2-hydroxypropyl(4-{[3-(4-fluorophenyl)-2-propynyl]amino}phenethyl)carbamate The title compound was prepared from tert-butyl 4-aminophenethyl{(2S)-3-[4-(benzyloxy)phenoxy]-2-hydroxypropyl}carbamate, and 1-(3-bromo-1-propynyl)-4-fluorobenzene (U.S. Pat. No. 5,574,051) in substantially the same manner, as described in example 25, step a. The product was obtained as a semi-solid: MS m/z 625 [M+H]$^+$.
Step b) 5-[(4-{2-[(2S)-3-(4-Benzyloxy-phenoxy)-2-hydroxy-propylamino]-ethyl}-phenyl)-[3-(4-fluoro-phenyl)-prop-2-ynyl]-amino}-thiazolidine-2,4-dione The title compound was prepared from tert-butyl (2S)-3-[4-(benzyloxy)phenoxy]-2-hydroxypropyl(4-{[3-(4-fluorophenyl)-2-propynyl]amino}phenethyl)carbamate, and 5-bromodiazolidine-2,4-dione in substantially the same manner, as described in example 4. The product was obtained as an off-white solid: mp: 99–101° C.; MS m/z 640 (M+H)$^+$; Analysis for $C_{36}H_{34}FN_3O_5S \times 0.27$ $H_2O \times 0.24$ $CF_3CO_2H$ Calc'd: C, 65.21; H, 5.22; N, 6.25; Found: C, 65.52; H, 5.25; N, 6.16.

EXAMPLE 28

5-[(4-Bromo-benzyl)-(4-{2-[(2S)-2-hydroxy-3-(4-hydroxy-phenoxy)-propylamino]-ethyl}-phenyl)-amino]-thiazolidine-2,4-dione
Step a) tert-Butyl 4-aminophenethyl[(2S)-2-hydroxy-3-(4-hydroxyphenoxy)propyl]carbamate A mixture of tert-butyl 4-aminophenethyl{(2S)-3-[4-(benzyloxy)phenoxy]-2-hydroxypropyl}carbamate (0.54 g, 1.1 mmol), and 10% Pd-C (0.05 g) in ethanol (30 mL) was hydrogenated at room temperature at 50 psi for 5.5 hours. Filtration and evaporation yielded an oil. MS m/z 401 (M−H)$^−$.
Step b) tert-Butyl 4-[(4-bromobenzyl)amino]phenethyl [(2S)-2-hydroxy-3-(4-hydroxyphenoxy)propyl]carbamate The title compound was prepared from tert-butyl 4-aminophenethyl[(2S)-2-hydroxy-3-(4-hydroxyphenoxy) propyl]carbamate and iodomethane in substantially the same manner, as described in example 4. The product was obtained as a white solid: MS m/z 571 [M+H]$^+$.
Step c) 5-[(4-Bromo-benzyl)-(4-{2-[(2S)-2-hydroxy-3-(4-hydroxy-phenoxy)-propylamino]-ethyl}-phenyl)-amino]-thiazolidine-2,4-dione The title compound was prepared from tert-butyl 4-[(4-bromobenzyl)amino]phenethyl[(2S)-2-hydroxy-3-(4-hydroxyphenoxy)propyl]carbamate, and 5-bromodiazolidine-2,4-dione in substantially the same manner, as described in example 4. The product was obtained as an off-white solid: mp: 79° C. (decomposed); MS m/z 584 (M−H)$^−$; Analysis for $C_{27}H_{28}BrN_3O_5S \times 0.59$ $H_2O \times 1.0$ $CF_3CO_2H$ Calc'd: C, 48.98; H, 4.28; N, 5.91; Found: C, 48.77; H, 4.32; N, 5.54.

EXAMPLE 29

5-((4-Bromo-benzyl)-{4-[2-((2S)-2-hydroxy-3-phenoxy-propylamino)-ethyl]-phenyl}-amino)-thiazolidine-2,4-dione
Step a) tert-Butyl 4-[(4-bromobenzyl)amino]phenethyl [(2S)-2-hydroxy-3-phenoxypropyl]carbamate A mixture of (2S)-1-[(4-aminophenethyl)amino]-3-phenoxy-2-propanol (0.503 g, 1.76 mmol), N,N-diisopropylethylamine (0.765 mL, 4.4 mmol) and di-tert-butyl dicarbonate (0.461 g, 2.11 mmol) in THF (11 mL) was stirred at room temperature under a nitrogen atmosphere for 3 hours. The reaction was quenched with saturated aqueous sodium bicarbonate and further diluted with water. The aqueous layer was extracted with ethyl acetate. The extract was washed with water, dried with MgSO$_4$ and concentrated to give a light brown solid (0.45 g, 66%). A mixture of this product (0.44 g, 1.14 mmol), 4-bromobenzyl bromide (0.58 g, 2.28 mmol) and potassium carbonate (0.31 g, 2.28 mmol) in acetone (6 mL) was stirred at room temperature for 6 hours. The mixture was diluted with water and extracted with ethyl acetate. The extract was washed with water and dried with MgSO$_4$. Evaporation and purification by flash column chromatography (hexane/ethyl acetate 7/3) gave an oil (0.33 g, 53%): mp: °C.; MS m/z 555 [M+H]$^+$.
Step b) 5-((4-Bromo-benzyl)-{4-[2-((2S)-2-hydroxy-3-phenoxy-propylamino)-ethyl]-phenyl}-amino)-thiazolidine-2,4-dione The title compound was prepared from tert-butyl 4-[(4-bromobenzyl)amino]phenethyl[(2S)-2-hydroxy-3-phenoxypropyl]carbamate, and 5-bromodiazolidine-2,4-dione in substantially the same manner, as described in example 4. The product was obtained as an off-white solid: mp: 52–54° C.; MS m/z 570 (M+H)$^+$; Analysis for $C_{27}H_{28}BrN_3O_4S \times 0.6$ $H_2O \times 1.5$ $CF_3CO_2H$ Calc'd: C, 47.89; H, 4.11; N, 5.59; Found: C, 47.54; H, 4.08; N, 5.22.

EXAMPLE 30

5-{4-[2-((2S)-2-Hydroxy-2-pyridin-3-yl-ethylamino)-ethyl]-phenylamino}-thiazolidine-2,4-dione
Step a) 3-[(2S)-Oxiranyl]pyridine A solution of borane-THF (1 M solution, 15 mL) was added dropwise to a 0° C., stirred solution of (S)-2-methyl-CBS-oxazaborolidine monohydrate (0.738 g, 2.5 mmol) in THF (10 mL) over a period of 10 min. After stirred at 0° C. for 10 minutes the mixture was then added dropwise into a cold (0° C.) stirred suspension of 3-(2-bromoacetyl)pyridine hydrobromide (7.0 g, 24.9 mmol) in THF (50 mL) over a period of 10 minutes. After addition was completed the mixture was stirred at room temperature under a nitrogen atmosphere overnight. The reaction was cooled to 0° C. and quenched with dry HCl (0.5 M in methanol, 9 mL) The mixture was further diluted with water and extracted with ethyl acetate. The extract was washed with water and dried with MgSO$_4$. Evaporation and purification by flash column chromatography (methylene chloride/methanol 95/5) gave (1 R)-2-bromo-1-(3-pyridinyl)-1-ethanol as a brown oil (1.72 g, 34%). This solid (1.71 g, 8.5 mmol) was dissolved in THF (15 mL) and 5 N aqueous sodium hydroxide (30 mL) was added. After the solution was stirred at room temperature for 10 minutes, the mixture was diluted with water and extracted with methylene chloride. The extract was washed with water, dried with MgSO$_4$, and concentrated to give a white solid (0.72 g, 72%): MS m/z 122 (M+H)$^+$.
Step b) (1S)-2-[(4-Aminophenethyl)amino]-1-(3-pyridinyl)-1-ethanol The title compound was prepared from 3-[(2S)-oxiranyl] pyridine, and 2-(4-aminophenyl)ethylamine in substantially the same manner, as described in example 21, step b. The product was obtained as an off-white solid: 82–83° C.; MS m/z 258 (M+H)$^+$.

Step c) 5-{4-[2-((2S)-2-Hydroxy-2-pyridin-3-yl-ethylamino)-ethyl]-phenylamino}-thiazolidine-2,4-dione The title compound was prepared from (1S)-2-[(4-aminophenethyl)amino]-1-(3-pyridinyl)-1-ethanol, and 5-bromodiazolidine-2,4-dione in substantially the same manner, as described in example 21, step c. The product was obtained as a yellow solid: mp: 46–48° C.; MS m/z 373 (M+H)$^+$; Analysis for $C_{18}H_{20}N_4O_3S \times 1.5$ $H_2O \times 2.5$ $CF_3CO_2H \times 0.1$ $C_2H_5O$ Calc'd: C, 40.62; H, 3.86; N, 8.09; Found: C, 40.87; H, 3.67; N, 7.78.

EXAMPLE 31
5-{4-[2-((2R)-2-Hydroxy-2-pyridin-3-yl-ethylamino)-ethyl]-phenylamino}-thiazolidine-2,4-dione
Step a) 3-[(2R)-Oxiranyl]pyridine The title compound was prepared from 3-(2-bromoacetyl) pyridine hydrobromide, and (R)-2-methyl-CBS-oxazaborolidine monohydrate in substantially the same manner, as described in example 30, step a. The product was obtained as an oil. MS m/z 121 M$^+$.

Step b) (1R)-2-[(4-Aminophenethyl)amino]-1-(3-pyridinyl)-1-ethanol

The title compound was prepared from 3-[(2R)-oxiranyl] pyridine, and 2-(4-aminophenyl)ethylamine in substantially the same manner, as described in example 30, step b. The product was obtained as a light brown solid: MS m/z 258 (M+H)$^+$.

Step c) 5-{4-[2-((2R)-2-Hydroxy-2-pyridin-3-yl-ethylamino)-ethyl]-phenylamino}-thiazolidine-2,4-dione The title compound was prepared from (1R)-2-[(4-aminophenethyl)amino]-1-(3-pyridinyl)-1-ethanol, and 5-bromodiazolidine-2,4-dione in substantially the same manner, as described in example 30, step c. The product was obtained as a yellow solid: mp: 65–67° C.; MS m/z 373 (M+H)$^+$; Analysis for $C_{18}H_{20}N_4O_3S \times 1.26$ $H_2O \times 2.2$ $CF_3CO_2H$ Calc'd: C, 41.65; H, 3.86; N, 8.67; Found: C, 41.86; H, 3.81; N, 8.24.

What is claimed is:

1. A compound of formula I having the structure

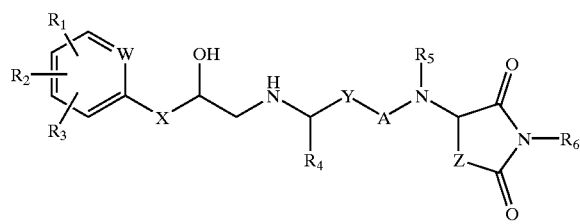

I wherein, $R_1$, $R_2$, $R_3$ are each, independently, hydrogen, alkyl of 1–6 carbon atoms, aryl of 6 to 10 carbon atoms, aryloxy of 6–10 carbon atoms, halogen, trifluoromethyl of 1–6 carbon atoms, arylalkoxy of 7–14 carbon atoms, arylalkyl of 7–14 carbon atoms, alkoxy of 1–6 carbon atoms, hydroxy, nitro, amino, aminocarbonyl, alkylamino of 1–6 carbon atoms, dialkyl amino of 1–6 carbon atoms per alkyl group, formamido, ureido, acyl of 2–7 carbon atoms, acylamino of 2–7 carbon atoms, amino, alkylsulfonylamino of 1–6 carbon atoms, or arylsulfonylamino of 6 to 10 carbon atoms; or two of $R_1$, $R_2$, and $R_3$ are taken together to form a phenyl ring or a heterocyclic ring which is fused to the ring which contains the $R_1$, $R_2$, or $R_3$ substituents, wherein the heterocyclic ring contains 1–3 heteroatoms selected from N, O, or S;

$R_4$ is hydrogen or alkyl of 1–6 carbon atoms;

$R_5$ is hydrogen, alkyl of 1–6 carbon atoms, aryl of 6–10 carbon atoms, arylalkyl of 7–14 carbon atoms, halogen substituted arylalkyl of 7–14 carbon atoms, arylalkene of 8–16 carbon atoms, arylalkyne of 8–16 carbon atoms, alkoxycarbonyl of 2–7 carbon atoms, aryloxycarbonyl of 7–11 carbon atoms, alkylsulfonyl of 1–6 carbon atoms, or arylsulfonyl of 1–6 carbon atoms;

$R_6$ is hydrogen, alkyl of 1–6 carbon atoms, aryl or arylalkyl of 7–14 carbon atoms;

A is phenyl, naphthyl, benzofuryl, or benzothienyl;

X is bond, —OCH$_2$—, or —SCH$_2$—;

Y is alkyl of 1–6 carbon atoms, or alkoxy of 1–6 carbon atoms;

W is nitrogen;

Z is carbon, sulfur, oxygen, or nitrogen;

or a pharmaceutically acceptable salt thereof.

2. The compound according to claim 1, wherein $R_1$, $R_2$, $R_3$ are each, independently, hydrogen, alkyl of 1–6 carbon atoms, aryl of 6 to 10 carbon atoms, aryloxy of 6–10 carbon atoms, halogen, arylalkoxy of 7–14 carbon atoms, arylalkyl of 7–14 carbon atoms, alkoxy of 1–6 carbon atoms, hydroxy, or alkylsulfonylamino of 1–6 carbon atoms; or two of $R_1$, $R_2$, and $R_3$ are taken together to form a heterocyclic ring which is fused to the ring which contains the $R_1$, $R_2$, or $R_3$ substituents, wherein the heterocyclic ring contains 1–3 heteroatoms selected from N, O, or S;

$R_4$ is hydrogen or alkyl of 1–6 carbon atoms;

$R_5$ is hydrogen, alkyl of 1–6 carbon atoms, halogen substituted arylalkyl of 7–14 carbon atoms, or arylalkyne of 8–16 carbon atoms;

$R_6$ is hydrogen, or alkyl of 1–6 carbon atoms;

A is phenyl, or benzofuryl;

X is bond, or —OCH$_2$—;

Y is alkyl of 1–6 carbon atoms;

Z is sulfur;

W is nitrogen;

or a pharmaceutically acceptable salt thereof.

3. The compound of claim 1, which is at least one of:

a) 5-{4-[2-((2S)-2-Hydroxy-2-pyridin-3-yl-ethylamino)-ethyl]-phenylamino}-thiazolidine-2,4-dione; or b) 5-{4-[2-((2R)-2-Hydroxy-2-pyridin-3-yl-ethylamino)-ethyl]-phenylamino}-thiazolidine-2,4-dione;

or a pharmaceutically acceptable salt thereof.

4. A method of treating metabolic disorders mediated by insulin resistance or hyperglycemia in a mammal in need thereof comprising treating said mammal with an effective amount of a compound of formula I having the structure

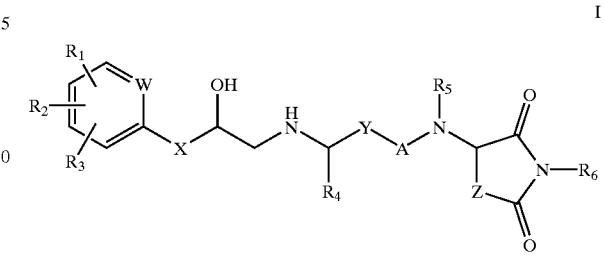

I wherein, $R_1$, $R_2$, $R_3$ are each, independently, hydrogen, alkyl of 1–6 carbon atoms, aryl of 6 to 10 carbon atoms, aryloxy of 6–10 carbon atoms, halogen, trifluoromethyl of 1–6 carbon atoms, arylalkoxy of 7–14 carbon atoms, arylalkyl of 7–14 carbon atoms, alkoxy of 1–6 carbon atoms, hydroxy, nitro, amino, aminocarbonyl, alkylamino of 1–6 carbon atoms, dialkyl amino of 1–6 carbon atoms per alkyl group, formamido, ureido, acyl of 2–7 carbon atoms, acylamino of 2–7 carbon atoms, amino, alkylsulfonylamino of 1–6 carbon atoms, or arylsulfonylamino of 6 to 10 carbon atoms; or two of $R_1$, $R_2$, and $R_3$ are taken together to form a phenyl ring or a heterocyclic ring which is fused to the ring which contains the $R_1$, $R_2$, or $R_3$ substituents, wherein the heterocyclic ring contains 1–3 heteroatoms selected from N, O, or S;

$R_4$ is hydrogen or alkyl of 1–6 carbon atoms;

$R_5$ is hydrogen, alkyl of 1–6 carbon atoms, aryl of 6–10 carbon atoms, arylalkyl of 7–14 carbon atoms, halogen substituted arylalkyl of 7–14 carbon atoms, arylalkene of 8–16 carbon atoms, arylalkyne of 8–16 carbon atoms, alkoxycarbonyl of 2–7 carbon atoms, aryloxycarbonyl of 7–11 carbon atoms, alkylsulfonyl of 1–6 carbon atoms, or arylsulfonyl of 1–6 carbon atoms;

$R_6$ is hydrogen, alkyl of 1–6 carbon atoms, aryl or arylalkyl of 7–14 carbon atoms;

A is phenyl, naphthyl, benzofuryl, or benzothienyl;

X is bond, —$OCH_2$—, or —$SCH_2$—;

Y is alkyl of 1–6 carbon atoms, or alkoxy of 1–6 carbon atoms;

W is nitrogen;

Z is carbon, sulfur, oxygen, or nitrogen or a pharmaceutically acceptable salt thereof.

5. A method of treating or inhibiting type II diabetes in a mammal in need thereof comprising treating said mammal with an effective amount of a compound of Formula I having the structure

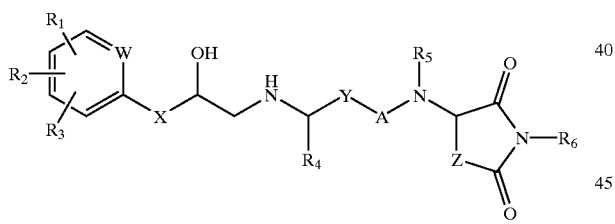

I wherein, $R_1$, $R_2$, $R_3$ are each, independently, hydrogen, alkyl of 1–6 carbon atoms, aryl of 6 to 10 carbon atoms, aryloxy of 6–10 carbon atoms, halogen, trifluoromethyl of 1–6 carbon atoms, arylalkoxy of 7–14 carbon atoms, arylalkyl of 7–14 carbon atoms, alkoxy of 1–6 carbon atoms, hydroxy, nitro, amino, aminocarbonyl, alkylamino of 1–6 carbon atoms, dialkyl amino of 1–6 carbon atoms per alkyl group, formamido, ureido, acyl of 2–7 carbon atoms, acylamino of 2–7 carbon atoms, amino, alkylsulfonylamino of 1–6 carbon atoms, or arylsulfonylamino of 6 to 10 carbon atoms; or two of $R_1$, $R_2$, and $R_3$ are taken together to form a phenyl ring or a heterocyclic ring which is fused to the ring which contains the $R_1$, $R_2$, or $R_3$ substituents, wherein the heterocyclic ring contains 1–3 heteroatoms selected from N, O, or S;

$R_4$ is hydrogen or alkyl of 1–6 carbon atoms;

$R_5$ is hydrogen, alkyl of 1–6 carbon atoms, aryl of 6–10 carbon atoms, arylalkyl of 7–14 carbon atoms, halogen substituted arylalkyl of 7–14 carbon atoms, arylalkene of 8–16 carbon atoms, arylalkyne of 8–16 carbon atoms, alkoxycarbonyl of 2–7 carbon atoms, aryloxycarbonyl of 7–11 carbon atoms, alkylsulfonyl of 1–6 carbon atoms, or arylsulfonyl of 1–6 carbon atoms;

$R_6$ is hydrogen, alkyl of 1–6 carbon atoms, aryl or arylalkyl of 7–14 carbon atoms;

A is phenyl, naphthyl, benzofuryl, or benzothienyl;

X is bond, —$OCH_2$—, or —$SCH_2$—;

Y is alkyl of 1–6 carbon atoms, or alkoxy of 1–6 carbon atoms;

W is nitrogen;

Z is carbon, sulfur, oxygen, or nitrogen;

or a pharmaceutically acceptable salt thereof.

6. A method of modulating glucose levels in a mammal in need thereof comprising treating said mammal with an effective amount of a compound of formula I having the structure

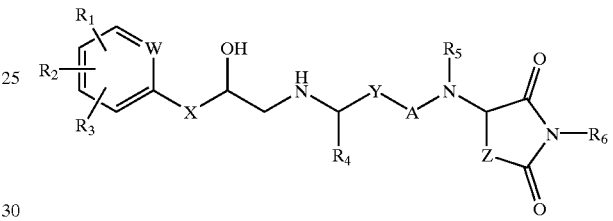

I wherein, $R_1$, $R_2$, $R_3$ are each, independently, hydrogen, alkyl of 1–6 carbon atoms, aryl of 6 to 10 carbon atoms, aryloxy of 6–1 0 carbon atoms, halogen, trifluoromethyl of 1–6 carbon atoms, arylalkoxy of 7–14 carbon atoms, arylalkyl of 7–14 carbon atoms, alkoxy of 1–6 carbon atoms, hydroxy, nitro, amino, aminocarbonyl, alkylamino of 1–6 carbon atoms, dialkyl amino of 1–6 carbon atoms per alkyl group, formamido, ureido, acyl of 2–7 carbon atoms, acylamino of 2–7 carbon atoms, amino, alkylsulfonylamino of 1–6 carbon atoms, or arylsulfonylamino of 6 to 10 carbon atoms; or two of $R_1$, $R_2$, and $R_3$ are taken together to form a phenyl ring or a heterocyclic ring which is fused to the ring which contains the $R_1$, $R_2$, or $R_3$ substituents, wherein the heterocyclic ring contains 1–3 heteroatoms selected from N, O, or S;

$R_4$ is hydrogen or alkyl of 1–6 carbon atoms;

$R_5$ is hydrogen, alkyl of 1–6 carbon atoms, aryl of 6–10 carbon atoms, arylalkyl of 7–14 carbon atoms, halogen substituted arylalkyl of 7–14 carbon atoms, arylalkene of 8–16 carbon atoms, arylalkyne of 8–16 carbon atoms, alkoxycarbonyl of 2–7 carbon atoms, aryloxycarbonyl of 7–11 carbon atoms, alkylsulfonyl of 1–6 carbon atoms, or arylsulfonyl of 1–6 carbon atoms;

$R_6$ is hydrogen, alkyl of 1–6 carbon atoms, aryl or arylalkyl of 7–14 carbon atoms;

A is phenyl, naphthyl, benzofuryl, or benzothienyl;

X is bond, —$OCH_2$—, or —$SCH_2$—;

Y is alkyl of 1–6 carbon atoms, or alkoxy of 1–6 carbon atoms;

W is nitrogen;

Z is carbon, sulfur, oxygen, or nitrogen or a pharmaceutically acceptable salt thereof.

7. A method of treating or inhibiting urinary incontinence in a mammal in need thereof comprising treating said mammal with an effective amount of a compound of formula I having the structure

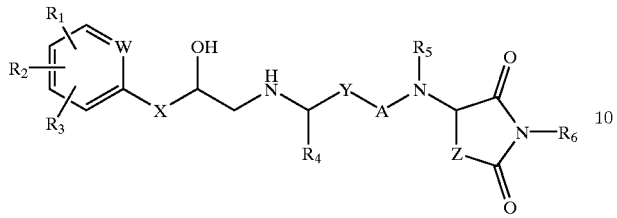

wherein, $R_1, R_2, R_3$ are each, independently, hydrogen, alkyl of 1–6 carbon atoms, aryl of 6 to 10 carbon atoms, aryloxy of 6–10 carbon atoms, halogen, trifluoromethyl of 1–6 carbon atoms, arylalkoxy of 7–14 carbon atoms, arylalkyl of 7–14 carbon atoms, alkoxy of 1–6 carbon atoms, hydroxy, nitro, amino, aminocarbonyl, alkylamino of 1–6 carbon atoms, dialkyl amino of 1–6 carbon atoms per alkyl group, formamido, ureido, acyl of 2–7 carbon atoms, acylamino of 2–7 carbon atoms, amino, alkylsulfonylamino of 1–6 carbon atoms, or arylsulfonylamino of 6 to 10 carbon atoms; or two of $R_1, R_2$, and $R_3$ are taken together to form a phenyl ring or a heterocyclic ring which is fused to the ring which contains the $R_1$, $R_2$, or $R_3$ substituents, wherein the heterocyclic ring contains 1–3 heteroatoms selected from N, O, or S;

$R_4$ is hydrogen or alkyl of 1–6 carbon atoms;

$R_5$ is hydrogen, alkyl of 1–6 carbon atoms, aryl of 6–10 carbon atoms, arylalkyl of 7–14 carbon atoms, halogen substituted arylalkyl of 7–14 carbon atoms, arylalkene of 8–16 carbon atoms, arylalkyne of 8–16 carbon atoms, alkoxycarbonyl of 2–7 carbon atoms, aryloxycarbonyl of 7–11 carbon atoms, alkylsulfonyl of 1–6 carbon atoms, or arylsulfonyl of 1–6 carbon atoms;

$R_6$ is hydrogen, alkyl of 1–6 carbon atoms, aryl or arylalkyl of 7–14 carbon atoms;

A is phenyl, naphthyl, benzofuryl, or benzothienyl;

X is bond, —OCH$_2$—, or —SCH$_2$—;

Y is alkyl of 1–6 carbon atoms, or alkoxy of 1–6 carbon atoms;

W is nitrogen;

Z is carbon, sulfur, oxygen, or nitrogen;

or a pharmaceutically acceptable salt thereof.

8. A method of treating or inhibiting atherosclerosis, gastrointestinal disorders, neurogenetic inflammation, glaucoma, or ocular hypertension in a mammal in need thereof, comprising treating said mammal with an effective amount of a compound of formula I having the structure

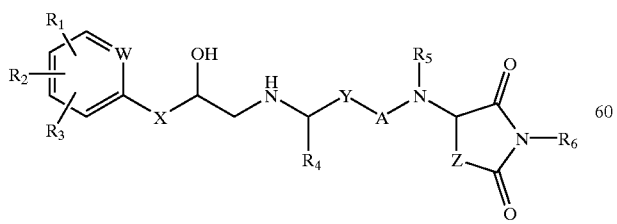

wherein, $R_1, R_2, R_3$ are each, independently, hydrogen, alkyl of 1–6 carbon atoms, aryl of 6 to 10 carbon atoms, aryloxy of 6–10 carbon atoms, halogen, trifluoromethyl of 1–6 carbon atoms, arylalkoxy of 7–14 carbon atoms, arylalkyl of 7–14 carbon atoms, alkoxy of 1–6 carbon atoms, hydroxy, nitro, amino, aminocarbonyl, alkylamino of 1–6 carbon atoms, dialkyl amino of 1–6 carbon atoms per alkyl group, formamido, ureido, acyl of 2–7 carbon atoms, acylamino of 2–7 carbon atoms, amino, alkylsulfonylamino of 1–6 carbon atoms, or arylsulfonylamino of 6 to 10 carbon atoms; or two of $R_1, R_2$, and $R_3$ are taken together to form a phenyl ring or a heterocyclic ring which is fused to the ring which contains the $R_1$, $R_2$, or $R_3$ substituents, wherein the heterocyclic ring contains 1–3 heteroatoms selected from N, O, or S;

$R_4$ is hydrogen or alkyl of 1–6 carbon atoms;

$R_5$ is hydrogen, alkyl of 1–6 carbon atoms, aryl of 6–10 carbon atoms, arylalkyl of 7–14 carbon atoms, halogen substituted arylalkyl of 7–14 carbon atoms, arylalkene of 8–16 carbon atoms, arylalkyne of 8–16 carbon atoms, alkoxycarbonyl of 2–7 carbon atoms, aryloxycarbonyl of 7–11 carbon atoms, alkylsulfonyl of 1–6 carbon atoms, or arylsulfonyl of 1–6 carbon atoms;

$R_6$ is hydrogen, alkyl of 1–6 carbon atoms, aryl or arylalkyl of 7–14 carbon atoms;

A is phenyl, naphthyl, benzofuryl, or benzothienyl;

X is bond, —OCH$_2$—, or —SCH$_2$—;

Y is alkyl of 1–6 carbon atoms, or alkoxy of 1–6 carbon atoms;

W is nitrogen;

Z is carbon, sulfur, oxygen, or nitrogen;

or a pharmaceutically acceptable salt thereof.

9. A pharmaceutical composition comprising:

a) an effective amount of a compound of formula I having the structure

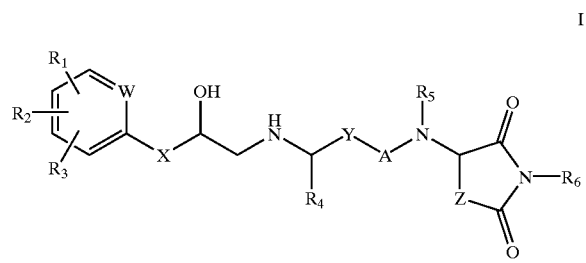

wherein, $R_1, R_2, R_3$ are each, independently, hydrogen, alkyl of 1–6 carbon atoms, aryl of 6 to 10 carbon atoms, aryloxy of 6–10 carbon atoms, halogen, trifluoromethyl of 1–6 carbon atoms, arylalkoxy of 7–14 carbon atoms, arylalkyl of 7–14 carbon atoms, alkoxy of 1–6 carbon atoms, hydroxy, nitro, amino, aminocarbonyl, alkylamino of 1–6 carbon atoms, dialkyl amino of 1–6 carbon atoms per alkyl group, formamido, ureido, acyl of 2–7 carbon atoms, acylamino of 2–7 carbon atoms, amino, alkylsulfonylamino of 1–6 carbon atoms, or arylsulfonylamino of 6 to 10 carbon atoms; or two of $R_1, R_2$, and $R_3$ are taken together to form a phenyl ring or a heterocyclic ring which is fused to the ring which contains the $R_1$, $R_2$, or $R_3$ substituents, wherein the heterocyclic ring contains 1–3 heteroatoms selected from N, O, or S;

$R_4$ is hydrogen or alkyl of 1–6 carbon atoms;

$R_5$ is hydrogen, alkyl of 1–6 carbon atoms, aryl of 6–10 carbon atoms, arylalkyl of 7–14 carbon atoms, halogen substituted arylalkyl of 7–14 carbon atoms, arylalkene of 8–16 carbon atoms, arylalkyne of 8–16 carbon atoms, alkoxycarbonyl of 2–7 carbon atoms, aryloxycarbonyl of 7–11 carbon atoms, alkylsulfonyl of 1–6 carbon atoms, or arylsulfonyl of 1–6 carbon atoms;

$R_6$ is hydrogen, alkyl of 1–6 carbon atoms, aryl or arylalkyl of 7–14 carbon atoms;

A is phenyl, naphthyl, benzofuryl, or benzothienyl;

X is bond, —$OCH_2$—, or —$SCH_2$—;

Y is alkyl of 1–6 carbon atoms, or alkoxy of 1–6 carbon atoms;

W is nitrogen;

Z is carbon, sulfur, oxygen, or nitrogen or a pharmaceutically acceptable salt thereof; and b) at least one pharmaceutical carrier.

\* \* \* \* \*